United States Patent [19]

Kawakita et al.

[11] Patent Number: 5,616,581
[45] Date of Patent: Apr. 1, 1997

[54] PHARMACEUTICAL USE OF PYRIDINE COMPOUNDS

[75] Inventors: Takeshi Kawakita; Mitsuharu Sano; Yuko Yutoku; Yoshifumi Ikeda; Keiichiro Haga, all of Chikujo-gun, Japan

[73] Assignee: Yoshitomi Pharmaceutical Industries, Ltd., Japan

[21] Appl. No.: 460,666

[22] Filed: Jun. 2, 1995

Related U.S. Application Data

[62] Division of Ser. No. 352,183, filed as PCT/JP93/00732, May 31, 1993, and a continuation-in-part of PCT/JP94/01800, Oct. 26, 1994, Pat. No. 5,504,082.

[30] Foreign Application Priority Data

Jun. 1, 1992 [JP] Japan .................................. 4-167017
Oct. 29, 1993 [JP] Japan .................................. 5-272494

[51] Int. Cl.⁶ .......................... A61K 31/44; A61K 31/535
[52] U.S. Cl. ...................... 514/234.5; 514/253; 514/307; 514/318; 514/338; 514/310; 514/233.8; 514/228.2
[58] Field of Search .................... 514/234.5, 253, 514/307, 318, 338

[56] References Cited

U.S. PATENT DOCUMENTS

| | | |
|---|---|---|
| 4,746,667 | 5/1988 | Carlsson et al. . |
| 5,013,743 | 5/1991 | Iwahi et al. . |
| 5,039,806 | 8/1991 | Brändström et al. . |
| 5,045,552 | 9/1991 | Souda et al. . |
| 5,093,342 | 3/1992 | Tomoi et al. . |
| 5,504,082 | 4/1996 | Kawakita et al. ................ 546/118 |

FOREIGN PATENT DOCUMENTS

| | | |
|---|---|---|
| 0533264A1 | 3/1993 | European Pat. Off. . |
| 0567643A1 | 11/1993 | European Pat. Off. . |
| 0585722A1 | 3/1994 | European Pat. Off. . |
| WO92/12976 | 8/1992 | WIPO . |
| WO9413290 | 6/1994 | WIPO . |

OTHER PUBLICATIONS

Suerbraum et al., *Eur. J. Clin. Microbiol. Infect. Dis.*, 10(2), 92–93 (1991).
Derwent Publications, Ltd., Abstract No. B0186 (1994) (abstract of JP 06100449–A).
Derwent Publications, Ltd., Abstract No. B0200 (1991) (abstract of JO 3038523A).
Derwent Publications, Ltd., Abstract No. B0205 (1991) (abstract of JO 3048680A).
Derwent Publications, Ltd., Abstract No. B0143 (1991) (abstract of JO 3052887A).
Derwent Publications, Ltd., Abstract No. B0125 (1991) (abstract of JO 3052812A).

*Primary Examiner*—Robert W. Ramsuer
*Attorney, Agent, or Firm*—Wenderoth, Lind & Ponack

[57] ABSTRACT

A pyridine compound of the formula

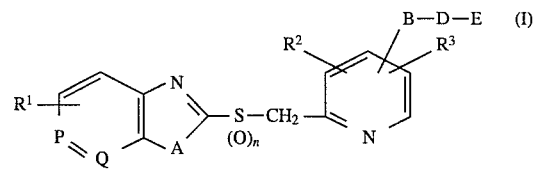

wherein $R^1$ is a hydrogen, a halogen, an alkyl, an alkoxy or the like, $R^2$ and $R^3$ are each a hydrogen, a halogen or an alkyl, —P=Q— is —CH=CH—, —N=CH— or —CH=N—, A is an oxygen atom, a sulfur atom or $N(R^4)$ wherein $R^4$ is hydrogen, alkyl or the like, n is 0, 1 or 2, B is S(O)p wherein p is 0, 1 or 2, D is a single bond, an alkylene or the like and E is an alkoxyalkyl or —N(R⁶)(R⁷), and a pharmaceutically acceptable salt thereof have antibacterial activity against *Helicobacter pylori*, antiulcer activity, gastrointestinal cytoprotective activity, ulcer recurrence, relapse-preventive activity and gastric acid secretion-suppressive activity and are useful as pharmaceutical preparations.

4 Claims, No Drawings

PHARMACEUTICAL USE OF PYRIDINE COMPOUNDS

This is a divisional application of Ser. No. 08/352,183, filed Dec. 1, 1994 now U.S. Pat. No. 5,504,082; which is a continuation-in-part of PCT/JP93/00732, filed May 31, 1993 and PCT/JP94/01800, filed Oct. 26, 1994.

FIELD OF THE INVENTION

The present invention relates to a novel pyridine compound having antiulcer activity, gastrointestinal cytoprotective activity, ulcer recurrence or relapse-preventive activity, gastric acid secretion-suppressive activity, antibacterial activity against *Helicobacter pylori* and the like, a pharmaceutically acceptable salt thereof and pharmaceutical use thereof.

BACKGROUND OF THE INVENTION

*Helicobacter pylori* (hereinafter sometimes referred to as *H. pylori*) is a Gram negative bacterium isolated from tunica mucosa ventriculi of a patient with active chronic gastritis (Warren, J. R. & Marshall, B. J. Lancet i, 1273–1275, 1983). *H. Pylori* is a 0.5 μm wide, 3–5 μm long Gram negative spirillar bacterium having several flagella and flagella sheaths at one pole or both poles. *H. pylori* grows under the microaerophillie environment, cannot grow under the aerobic conditions and grows poorly under the anaerobic conditions. It grows at 37° C. and scarcely grows at not higher than 25° C. and not lower than 42° C. The bacterium is notably characterized in that it evidently produces urease (Mobley, H. L. et al., Clin. Microbiol., 26, 831–836, 1988).

*H. pylori* is present in the mucous layer in the tunica mucosa ventriculi epithelium of humans and swims in the viscous mucous layer using peculiar flagella that the bacterium has. *H pylori* specifically resides in the cortical layer of the epithelium cells and the crevice therein, which provide the most comfortable living environment where gastric acidity is neutral, and lives by utilizing hemin, urea and so on (Hazell, S. L., Adrian, L., J. Infect. Dis., 153, 658–663, 1986).

As to the mechanism of the onset of diseases caused by *H. pylori*, mucous membrane disorder concept (Hazell, S. L., Adrian, L., J. Infect. Dis., 153, 658–663, 1986), leaking roof concept (Goodwin C. S., Lancet ii, 1467–1469, 1988) and gastrin link concept (Levi, S. et al., Lancet i, 1167–1168, 1989) have been proposed.

The mucous membrane disorder caused by *H. pylori* is mostly ascribed to a strong urease activity (Hazell, S. L., Adrian, L., J. Infect. Dis., 153, 658–663, 1986). The urea present in the gastric juice is decomposed by the urease of *H. pylori* to produce a large amount of ammonium and carbon dioxide. The ammonium concentration in the gastric juice is significantly high in the group that tested positive to *H. pylori* and histological epitheliocyte disorder and increased ulcer coefficient have also been reported from a test where ammonium was orally administered to rats (Murakami, M. et al., Clin. Gastroenterol., 12 (Suppl. 1), S104–109, 1990). Also, there is a report on reduced amounts of PAS (periodic acid schiff)-positive mucosal juice in the tunica mueosa ventriculi of the patients who tested positive to *H. pylori*, suggesting possible degradation in the tunica mucosa ventriculi-protective activity due to the decomposition of mucosal juice by the protease of *H. pylori* (Nakajima, M. et al., Drug Investigation, 2 (Suppl. 1), 60, 1990). It has been further reported that leukotriene B4 activity is high in the tunlea mucosa ventriculi where prominent *H. pylori*-positive leukocyte infiltration is observed (Uchida, T. et al., Therapeutic Research, 12, 85–90, 1991) and that the mucous membrane disorder is caused by the action of phospholipase A2 on bile acid which flows reversely into the stomach. In 1988, Leunk et al. reported the presence of a cytovacuolating toxin in the supernatant of *H. pylori* culture. The toxin was isolated and purified by Cover et al (Cover, T. L. & Blaser, M. J., J. Biol. Chem. 267, 10570–10575, 1992). There are reports on the toxin that it delays cure of ulcer by hindering the rotation of cells near the ulcer (Chang, K. et al., Gastroenterology, 104 (Suppl.), A52, 1993) and that it acts synergistically with ammonium on cytovaeuolation (Sommi, P. et al., Gastroenterology, 104 (Suppl.), A196, 1993). In recent years, disorder of tunica mucosa ventriculi, which is caused by acetoaldehyde produced in the stomach by the alcohol dehydrogenase activity possessed by *H. pylori* (Salmela, K. S. et al., Gastroenterology, 105, 325–330, 1990), monochloramine produced in the presence of ammonium (Saida, H. et al., Nikon Shokakibyo Gakkai Zasshi 90, 1949, 1993) and interleukin 8 (Crowe, S. E. et al., Gastroenterology, 104, A687, 1993) have been drawing attention.

With regard to the relationship between peptic ulcer and *H. pylori*, the involvement of *H. pylori* has been strongly suggested in view of the very high segregation frequency of *H. pylori*, particularly in duodenal ulcer, and infection with *H. pylori* is considered to be deeply concerned with prolonged cure and recurrence of peptic ulcer (see, for example, Raws EAJ, et al., Gastroenterology, 94, 33–40, 1988).

With regard to the relationship between gastritis and *H. pylori*, the causality has been suggested based on oral infection tests in human (Morris, A. & Nicholoson, G. Am., J. Gastroenterology, 82, 192–199, 1987, Marshall, B. J. et al., Med. J. Aust., 142, 436–439, 1985). The segregation frequency of *H. pylori* from gastritis is high and the correlation between the cell number of *H. pylori*, and the increase in neutrophilic leukocytes (which is an index of activeness of gastritis) and the degree of clinical symptoms accompanied by infiltration of lymphocyte has been confirmed. Moreover, development of gastritis in vestibulum of stomach with flare and erosion has been endoscopically observed in animal tests using Japanese monkeys (Shuto, R. et al., Infect. Immun., 61, 1,933–939, 1993).

The number of reports on the onset of stomach tumor, which begins with persistent infection of *H. pylori* via atrophic gastritis and intestinal metaplasia is recently on the rise. In 1991, Parsonnet et al. determined the IgG antibody titer of anti-*H. pylori* using a serum preserved for about 25 years and found a strong correlation between stomach tumor and patients having the antibody. It has been also found, by epidemiological studies, that morbidity of and death from stomach tumor are high in the area where *H. pylori* antibody positive ratio is high (Parsonnet, J. et al., N. Engl. J. Med., 325, 1127–1131, 1991).

The treatment of stomach ulcer and duodenal ulcer has made a remarkable progress over the recent years. However, the problems remain that they are susceptible to recurrence when drugs therefor are reduced or withdrawn and that an intractable ulcer having resistance to drugs may be developed. With the prevailing indication of the involvement of *H. pylori* in stomach and duodenal ulcers, eradication of *H. pylori* by the administration of drugs having antibacterial activity against *H. pylori* has become the target of investigation (Chiba, N. et al., Am. J. Gastroenterology, 87, 1716–1727, 1992).

The antibacterial activity against *H. pylori* is particularly prominent in amoxieillin and clarithromycin from among the antibacterial drugs. While the antibacterial activity can be also found in such antiprotozoals as metronidazole and tinidazole, resistance to these drugs is known to be acquired at a rather early stage. Of the antiulcer drugs, proton pump inhibitors such as omeprazole show weak antibacterial activity, whereas H2 receptor antagonists such as cimetidine, ranitidine and famotidine fail to show such activity. The drugs having an antibacterial activity exhibit only weak clinical effects by single administration. Therefore, administration of plural antibacterial drugs, dual therapy concurrently using a bismuth preparation and an antibacterial drug, or triple therapy using a bismuth preparation and two antibacterial drugs has been tried. Yet, these therapeutic methods rather frequently cause side effects such as diarrhea and abdominal distension.

There are many reports supporting the effectiveness of the eradication of *H. pylori* and they agree on a conclusion that the eradieation resulted in cure of intractable ulcer and suppression of ulcer recurrence.

Raws et al. achieved 88% eradication by the concurrent use of three drugs of bismuth subeitrate, amoxieillin and metronidazole and 6% recurrence ratio one year thereafter (Raws EAJ, et al., Gastroenterology, 94, 33–40, 1988). Moreover, Graham et al. reportedly used three drugs of bismuth subeitrate, tetraeycline and metronidazole along with the treatment using ranitidine and achieved eradication in 89% of the ulcer eases and recurrence ratio after one year of 12% in duodenal ulcer and 13% in stomach ulcer, which ratios being remarkably lower than the recurrence ratios of 95% and 74% after the treatment solely with ranitidine (Graham, D. Y. et al., Shok aki naishikyo, Vol. 4, 429–440, 1992). A therapy by the concurrent use of a proton pump inhibitor and an antibacterial drug has been tried in recent years and ulcer recurrence-preventive effect to the same degree as that achieved in the concurrent use of three antibacterial drugs was reportedly obtained (Fujioka, T. et al., Nihon Rinsyo, Vol. 51, 3255–3260, 1993).

Some report says that administration of an antibacterial drug for eradicating *H. pylori* to a patient with intractable ulcer, who failed to cure with H2 receptor antagonists, resulted in cure of the ulcer, thus suggesting a potential use of the administration as a treatment method as well as for the prevention of recurrence. As stated in the foregoing, the usefulness of eradicating *H. pylori* is evident, though many problems remain to be solved before complete eradication is achieved. For example, long-term administration of bismuth preparation, which is useful for the eradication of *H. pylori*, is not possible, due to diarrhea, nausea and side effects on central nervous system it causes, bismuth subcitrate is not approved as an antiulcer drug in Japan, side effects caused by the multiple drug therapy are frequently found, antibacterial drugs used for the multiple drug therapy amounts high, usable time periods of the antibacterial drugs have not been established yet and re-infection after the eradication of *H. pylori* is found. In view of the problems as described, an antiulcer drug having a strong selective antibacterial action on *H. pylori* and less side effects is desired. It is needless to say that a drug having an antibacterial action only against *H. pylori*, and gastric acid secretion suppressive action as well, is desirable from the aspect of ulcer curing.

Japanese Patent Unexamined Publication Nos. 209809/1990, 38523/1991, 48680/1991, 52887/1991, 52812/1991 and International Publication No. W092/12976 disclose compounds having antibacterial activity against *Helicobacter pylori*. A similar compound has been disclosed in Japanese Patent Unexamined Publication No. 100449/1994 which was published after the priority date of the present invention. A compound having more excellent activities than these compounds is demanded.

SUMMARY OF THE INVENTION

With the aim of solving the above-mentioned problems, the present inventors have conducted various studies and found a compound having not only selective and superior antibacterial activity against *Heticobacter pylori*, but also antiulcer activity, gastrointestinal eytoproteetive activity, ulcer recurrence or relapse-preventive activity and gastric acid secretion-suppressive activity, which resulted in the completion of the invention.

The present invention is as follows.

1. A pyridine compound of the formula (I)

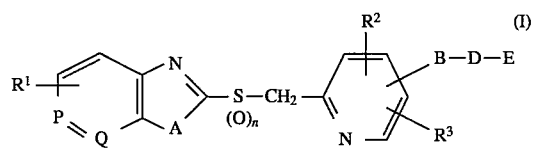

wherein $R^1$ is a hydrogen, a halogen, an alkyl, an alkoxy, a hydroxyl, an alkoxycarbonyl, a carboxyl, a haloalkyl, a nitro, an amino, a mono- or dialkylamino, an alkoxycarbonylalkylamino or a carboxyalkylamino, $R^2$ and $R^3$ are the same or different and each is a hydrogen, a halogen or an alkyl, —P=Q— is —CH=CH—, —N=CH— or —CH=N—, A is an oxygen atom, a sulfur atom or $N(R^4)$ wherein $R^4$ is hydrogen, alkyl, alkoxycarbonyl, hydroxyalkyl, alkoxyalkyl, acyloxyalkyl, alkoxycarbonylalkyl, carboxyalkyl, carbamoyl, carbamoylalkyl, mono- or dialkylcarbamoyl, mono- or dialkylcarbamoylalkyl, thiocarbamoyl, or mono- or dialkylthiocarbamoyl, n is 0, 1 or 2, B is S(O)p wherein p is 0, 1 or 2, D is a single bond, an alkylene, an alkylene having substituent, an alkylene having oxo or $(L-O)_q$ wherein L is ethylene or vinylene and q is an integer of 1 to 1000, provided that when L is vinylene, q is 1, and E is an alkoxyalkyl, a group of the formula (a)

wherein $R^6$ and $R^7$ are the same or different and each is hydrogen, alkyl, cycloalkyl, acyl, alkoxycarbonyl, carbamoyl, mono- or dialkylcarbamoyl, optionally substituted phenylcarbamoyl, thiocarbamoyl, mono- or dialkylthiocarbamoyl, optionally substituted phenylthiocarbamoyl, hydroxyalkyl, alkoxycarbonylalkyl, optionally substituted phenylalkylcarbamoyl, optionally substituted phenylalkylthiocarbamoyl, carboxyalkyl, optionally substituted phenyl, optionally substituted phenylalkyl or optionally substituted heteroarylalkyl, or $R^6$ and $R^7$ may form, together with the adjoining nitrogen atom, an optionally condensed and optionally substituted heterocyclic ring, a group of the formula (b)

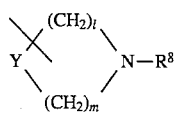

wherein R⁸ is hydrogen, alkyl, acyl, carboxyalkyl or optionally substituted phenylalkyl, Y is methylene, oxygen atom or sulfur atom and l and m are the same or different and each is 0 or an integer of 1–3, a hydrogen or an alkyl;

provided that when D is (L-O)$_q$, E is a hydrogen or an alkyl; or a pharmaceutically acceptable salt thereof.

2. A pharmaceutical composition comprising the pyridine compound of above 1 or a pharmaceutically acceptable salt thereof, and pharmaceutical additives.

3. An agent for preventing or treating various diseases caused by the bacteria belonging to the genus Helicobacter, which comprises the compound of above 1 or a pharmaceutically acceptable salt thereof as an active ingredient.

4. An agent for preventing or treating gastrointestinal diseases, which comprises the compound of above 1 or a pharmaceutically acceptable salt thereof as an active ingredient.

5. The pyridine compound of above 1, wherein the formula (I) is the following formula (I')

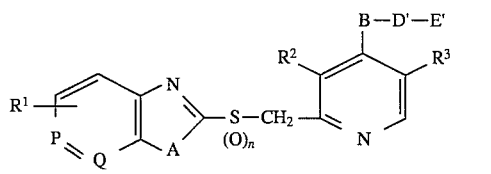

wherein

R¹ is a hydrogen, a halogen, an alkyl, an alkoxy, a hydroxyl, an alkoxycarbonyl, a carboxyl, a haloalkyl, a nitro, an amino, a mono- or dialkylamino, an alkoxycarbonylalkylamino or a carboxyalkylamino, R² and R³ are the same or different and each is a hydrogen, a halogen or an alkyl, —P=Q— is —CH=CH—, —N=CH— or —CH=N—, A is an oxygen atom, a sulfur atom or N(R⁴) wherein R⁴ is hydrogen, alkyl, alkoxycarbonyl, hydroxyalkyl, alkoxyalkyl, acyloxyalkyl, alkoxycarbonylalkyl, carboxyalkyl, carbamoyl, carbamoylalkyl, mono- or dialkylcarbamoyl, mono- or dialkylcarbamoylalkyl, thiocarbamoyl, or mono- or dialkylthiocarbamoyl, n is 0, 1 or 2, B is S(O)p wherein p is 0, 1 or 2, D' is a single bond, an alkylene, an alkylene having substituent or an alkylene having oxo, and E' is an alkoxyalkyl, a group of the formula (a)

wherein R⁶ and R⁷ are the same or different and each is hydrogen, alkyl, cycloalkyl, acyl, alkoxycarbonyl, carbamoyl, mono- or dialkylcarbamoyl, optionally substituted phenylcarbamoyl, thiocarbamoyl, mono- or dialkylthiocarbamoyl, optionally substituted phenylthiocarbamoyl, hydroxyalkyl, alkoxycarbonylalkyl, optionally substituted phenylalkylcarbamoyl, optionally substituted phenylalkylthiocarbamoyl, carboxyalkyl, optionally substituted phenyl, optionally substituted phenylalkyl or optionally substituted heteroarylalkyl, or R⁶ and R⁷ may form, together with the adjoining nitrogen atom, an optionally condensed and optionally substituted heterocyclic ring, or a group of the formula (b)

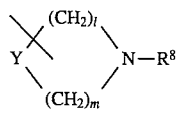

wherein R⁸ is hydrogen, alkyl, acyl, carboxyalkyl or optionally substituted phenylalkyl, Y is methylene, oxygen atom or sulfur atom and l and m are the same or different and each is 0 or an integer of 1–3;

or a pharmaceutically acceptable salt thereof.

6. The pyridine compound of above 5, which is selected from the group consisting of 2-((3-methyl-4-(2-morpholinoethylthio)-2-pyridyl)methylthio)-1H-benzimidazole, 2-((3-methyl-4-(2-(1,2,3,4-tetrahydroisoquinolin-2-yl)ethylthio)-2-pyridyl)methylthio)-1H-benzimidazole, 2-((4-(2-(N-benzyl-N-methylamino)ethyl thio)-3-methyl-2-pyridyl)methylthio)-1H-benzimidazole, 2-((4-(1-benzyl-4-piperidyl)thio-3-methyl-2-pyridyl)methylthio)-1H-benzimidazole, 2-((3-methyl-4-(2-(1,2,3,4-tetrahydroisoquinolin-2-yl)ethylthio)-2-pyridyl)methylthio)imidazo[5,4-b]pyridine, ethyl 2-((3-methyl-4-(2-morpholinoethylthio)-2-pyridyl)methylthio)-1H-benzimidazole-1-carboxylate, methyl 2-((3-methyl-4-(2-(1,2,3,4-tetrahydroisoquinolin-2-yl)ethylthio)-2-pyridyl)methylthio)-1H-benzimidazole-1-carboxylate, 4-(2-((2-(1H-benzimidazol-2-yl)thiomethyl-3-methyl-4-pyridyl)thio)ethyl)morpholine N-oxide, 2-((3-methyl-4-(2-acetylaminoethylthio)-2-pyridyl)methylthio)-1H-benzimidazole, 2-((3-methyl-4-(2-benzylaminoethylthio)-2-pyridyl)methylthio)-1H-benzimidazole, 2-((3-methyl-4-(2-(2-hydroxyethylamino)ethylthio)-2-pyridyl)methylthio)-1H-benzimidazole, 2-((3-methyl-4-(2-(N,N-di(2-hydroxyethyl)amino)ethylthio)-2-pyridyl)methylthio)-1H-benzimidazole, 2-((3-methyl-4-(2-(2-carboxyethylamino)ethylthio)-2-pyridyl)methylthio)-1H-benzimidazole, 2-((3-methyl-4-(2-morpholino-2-carboxyethylthio)-2-pyridyl)methylthio)-1H-benzimidazole, 2-((3-methyl-4-(2-dimethylaminoethylthio)-2-pyridyl)methylthio)-1H-benzimidazole and 2-((3-methyl-4-(2-(1-acetyl-2-methyl-4-piperazinyl)ethylthio)-2-pyridyl)methylthio)-1H-benzimidazole, or a pharmaceutically acceptable salt thereof.

7. A pharmaceutical composition comprising the compound of above 5 or a pharmaceutically acceptable salt thereof, and pharmaceutical additives.

8. An agent for preventing or treating various diseases caused by the bacteria belonging to the genus Helocibacter, which comprises the compound of above 5 or a pharmaceutically acceptable salt thereof as an active ingredient.

9. An agent for preventing or treating gastrointestinal diseases, which comprises the compound of above 5 or a pharmaceutically acceptable salt thereof as an active ingredient.

10. The pyridine compound of above 1, wherein the formula (I) is the following formula (I")

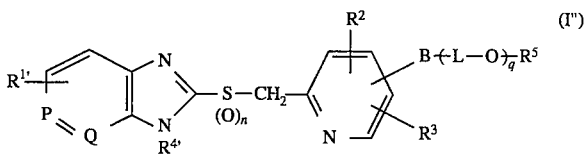
(I")

wherein
$R^{1'}$ is a hydrogen, a halogen, an alkyl, an alkoxy, a hydroxyl, an alkoxycarbonyl, a carboxyl or a haloalkyl,
$R^2$ and $R^3$ are the same or different and each is a hydrogen, a halogen or an alkyl,
$R^{4'}$ is a hydrogen, an alkoxycarbonyl, a hydroxyalkyl or an acyloxyalkyl,
$R^5$ is a hydrogen or an alkyl, —P=Q— is —CH=CH—, —N=CH— or —CH=N—, n is 0, 1 or 2,
B is S(O)p wherein p is 0, 1 or 2,
L is an ethylene or a vinylene, and
q is an integer of 1 to 1000, provided that when L is vinylene, q is 1,
or a pharmaceutically acceptable salt thereof.

11. The pyridine compound of above 10, wherein the formula (I") is the following formula (I"-a)

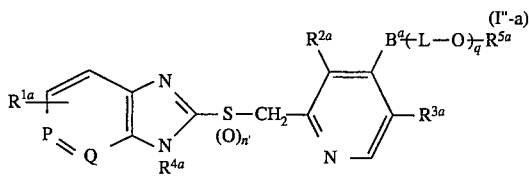
(I"-a)

wherein
$R^{1a}$ is a hydrogen, a halogen, an alkyl having 1 to 5 carbon atoms, an alkoxy having 1 to 5 carbon atoms or a hydroxyl,
$R^{2a}$ and $R^{3a}$ are the same or different and each is a hydrogen, or an alkyl having 1 to 5 carbon atoms,
$R^{4a}$ is a hydrogen,
$R^{5a}$ is a hydrogen or an alkyl having 1 to 8 carbon atoms, —P=Q— is —CH=CH—, —N=CH— or —CH=N—, n is 0 or 1,
$B^a$ is S,
L is an ethylene or a vinylene, and
q' is an integer of 1 to 100, provided that when L is vinylene, q' is 1,
or a pharmaceutically acceptable salt thereof.

12. The pyridine compound of above 10, wherein the formula (I") is the following formula (I"-b )

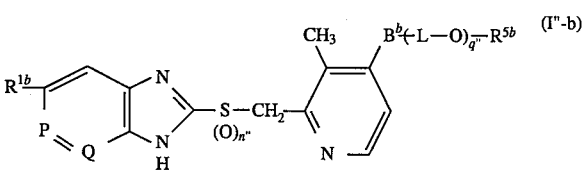
(I"-b)

wherein
$R^{1b}$ is a hydrogen, a halogen, an alkoxy having 1 to 3 carbon atoms or a hydroxyl, $R^{5b}$ is an alkyl having 1 to 5 carbon atoms, —P=Q— is —CH=CH—, —N=CH— or —CH=N—, n" is 0 or 1,
$B^b$ is S,
L is an ethylene or a vinylene, and
q" is an integer of 1 to 20, provided that when L is a vinylene, q" is 1,
or a pharmaceutically acceptable salt thereof.

13. The pyridine compound of above 10, which is selected from the group consisting of
2-((3-methyl-4-(2-(2-methoxyethoxy)ethylthio)-2-pyridyl)methylthio)-1H-benzimidazole,
2-((3-methyl-4-(2-(2-(2-methoxyethoxy)ethoxy)ethylthio)-2-pyridyl)methylthio)-1H-benzimidazole,
2-((3-methyl-4-(2-(2-(2-(2-methoxyethoxy)ethoxy)ethoxy)ethylthio)-2-pyridyl)methylthio)-1H-benzimidazole,
2-((3-methyl-4-(4,7,10,13,16-pentaoxa-1-thia-heptadecyl)-2-pyridyl)methylthio)-1H-benzimidazole,
2-((3-methyl-4-(2-(2-methoxypolyethoxy)ethylthio)-2-pyridyl)methylthio)-1H-benzimidazole derived from polyethylene glycol monomethyl ether having an average molecular weight of 350,
2-((3-methyl-4-(2-(2-methoxypolyethoxy)ethylthio)-2-pyridyl)methylthio)-1H-benzimidazole derived from polyethylene glycol monomethyl ether having an average molecular weight of 550,
2-((3-methyl-4-(2-(2-methoxypolyethoxy)ethylthio)-2-pyridyl)-methylsulfinyl)-1H-benzimidazole derived from polyethylene glycol monomethyl ether having an average molecular weight of 350,
trans-2-((3-methyl-4-(2-ethoxyvinylthio)-2-pyridyl)methylthio)-1H-benzimidazole and
2-((3-methyl-4-(2-(2-methoxypolyethoxy)ethylthio)-2-pyridyl)methylthio)-3H-imidazo[4,5-b]pyridine derived from polyethylene glycol monomethyl ether having an average molecular weight of 350,
or a pharmaceutically acceptable salt thereof.

14. A pharmaceutical composition comprising the compound of above 10 or a pharmaceutically acceptable salt thereof, and pharmaceutical additives.

15. An agent for preventing or treating various diseases caused by the bacteria belonging to the genus Helicobacter, which comprises the compound of above 10 or a pharmaceutically acceptable salt thereof as an active ingredient.

16. An agent for preventing or treating gastrointestinal diseases, which comprises the compound of above 10 or a pharmaceutically acceptable salt thereof as an active ingredient.

Specific examples of the respective groups in the formula (I) are as follows.

With regard to $R^1$, halogen is chlorine, fluorine, bromine or iodine, and alkyl may be straight or branched and has 1 to 20 carbon atoms, which is exemplified by methyl, ethyl, propyl, isopropyl, butyl, isobutyl, tert-butyl, pentyl, hexyl, octyl, decyl, dodecyl, octadecyl and icosyl, with preference given to alkyl having 1 to 5 carbon atoms. Alkoxy may be straight or branched and has 1 to 20 carbon atoms, which is exemplified by methoxy, ethoxy, propoxy, isopropoxy, butoxy, isobutoxy, tert-butoxy, pentyloxy, hexyloxy, octyloxy, decyloxy, dodecyloxy, octadecyloxy and icosyloxy, with preference given to alkoxy having 1 to 5 carbon atoms, more preference given to alkoxy having I to 3 carbon atoms. Alkoxycarbonyl may be straight or branched and has 1 to 21 carbon atoms, which is exemplified by methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, octyloxycarbonyl, decyloxycarbonyl, dodecyloxycarbonyl, octadecyloxycarbonyl and icosyloxycarbonyl. Haloalkyl may be straight or branched and has 1 to 4 carbon atoms, which is exemplified by trifluoromethyl, 2,2,2-trifluoroethyl, 2,3,3-trifluoropropyl, 1,1,2,2-tetrafluoroethyl and 2,2,3,3-tetrafluoropropyl. Mono- or dialkylamino is methylamino, dimethylamino, ethyl amino, diethylamino, propylamino, dipropylamino, butyl amino or dibutylamino, particularly mono- or di-$C_1$–$C_4$ alkylamino, alkoxycarbonylalkylamino is methoxycarbonylmethylamino, ethoxycarbonylmethylamino, propoxycarbonylmethylamino, isopropoxycarbonylmethylamino, butoxycarbonylmethylamino, isobutoxycarbonylmethylamino, tert-butoxycarbonylmethylamino, 2-methoxycarbonylethylamino or 2-ethoxycarbonylethylamino, particularly $C_1$–$C_4$ alkoxycarbonyl $C_1$–$C_4$ alkylamino, and carboxyalkylamino is carboxymethylamino, 2-carboxyethylamino, 3-carboxypropylamino or 4-carboxybutylamino, particularly carboxy $C_1$–$C_4$ alkylamino.

With regard to $R^2$ and $R^3$, halogen is chlorine, fluorine, bromine or iodine, alkyl is that having 1 to 4 carbon atoms, such as methyl, ethyl, propyl, isopropyl, butyl, isobutyl and tert-butyl, $R^2$ is preferably methyl and $R^3$ is preferably hydrogen or methyl.

With regard to $R^4$, alkyl is that having 1 to 20 carbon atoms, such as methyl, ethyl, propyl, isopropyl, butyl, isobutyl, tert-butyl, pentyl, hexyl, octyl, decyl, dodecyl, octadecyl and icosyl, alkoxycarbonyl is that having 2 to 21 carbon atoms, such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, octyloxycarbonyl, decyloxycarbonyl, dodecyloxycarbonyl, octadecyloxycarbonyl and icosyloxycarbonyl, hydroxyalkyl is that having 1 to 4 carbon atoms, such as hydroxymethyl, 1-hydroxyethyl, 2-hydroxyethyl, 3-hydroxypropyl, 2,3-dihydroxypropyl and 4-hydroxybutyl, and alkoxyalkyl is methoxymethyl, ethoxymethyl, propoxymethyl, isopropoxymethyl, butoxymethyl, isobutoxymethyl, tert-butoxymethyl, 2-methoxyethyl, 2-ethoxyethyl, 3-methoxypropyl or 4-methoxybutyl, particularly $C_1$–$C_4$ alkoxy $C_1$–$C_4$ alkyl. Acyloxyalkyl is that wherein acyl moiety has 1 to 7 carbon atoms and alkyl moiety has 1 to 4 carbon atoms, which is exemplified by acetyloxymethyl, propionyloxymethyl, 2-acetyloxyethyl, 3-acetyloxypropyl, 4-acetyloxybutyl, benzoyloxymethyl, 2-benzoyloxyethyl, or benzoyloxymethyl or 2-benzoyloxyethyl substituted by 1 to 3 substituents selected from halogen, alkyl, alkoxy, haloalkyl, hydroxyl, nitro and amino on the benzene ring. Examples of halogen, alkyl, alkoxy and haloalkyl are those mentioned above for $R^1$. Alkoxycarbonylalkyl is methoxycarbonylmethyl, ethoxycarbonylpropyl, propoxycarbonylethyl, isopropoxycarbonylethyl, butoxycarbonylmethyl, isobutoxycarbonylethyl, tert-butoxycarbonylmethyl, pentyloxycarbonylmethyl, hexyloxycarbonylmethyl, octyloxycarbonylmethyl, decyloxycarbonylethyl, dodecyloxycarbonylmethyl, octadecyloxycarbonylmethyl or icosyloxycarbonylmethyl, particularly $C_1$–$C_{20}$ alkoxycarbonyl $C_1$–$C_4$ alkyl. Carboxyalkyl is that having 1 to 5 carbon atoms, such as carboxymethyl, 2-carboxyethyl, 3-carboxypropyl and 4-carboxybutyl.

Carbamoylalkyl is carbamoylmethyl, 2-carbamoylethyl, 3-carbamoylpropyl or 4-carbamoylbutyl, particularly carbamoyl $C_1$–$C_4$ alkyl. Mono- or dialkylcarbamoyl is carbamoyl substituted by alkyl at its nitrogen atom, such as N-methylcarbamoyl, N,N-dimethylcarbamoyl, N-ethylcarbamoyl, N,N-diethylcarbamoyl, N-propylcarbamoyl, N,N-dipropylcarbamoyl, N-isopropylcarbamoyl and N-butylcarbamoyl, particularly mono- or di-$C_1$–$C_4$ alkylcarbamoyl. Mono- or dialkylcarbamoylalkyl is carbamoyl substituted by alkyl at its nitrogen atom, such as N-methylcarbamoylmethyl, N,N-dimethylcarbamoylmethyl, N-ethylcarbamoylmethyl, N,N-diethylcarbamoylmethyl, N-propylcarbamoylmethyl, N,N-dipropylcarbamoylmethyl, N-isopropylcarbamoylmethyl and N-butylcarbamoylmethyl, particularly mono- or di-$C_1$–$C_4$ alkylcarbamoyl $C_1$–$C_4$ alkyl. Mono- or dialkylthiocarbamoyl is thiocarbamoyl substituted by alkyl at its nitrogen atom, such as N-methylthiocarbamoyl, N,N-dimethylthiocarbamoyl, N-ethylthiocarbamoyl, N,N-diethylthiocarbamoyl, N-propylthiocarbamoyl, N,N-dipropylthiocarbamoyl, N-isopropylthiocarbamoyl and N-butylthiocarbamoyl, particularly mono- or di-$C_1$–$C_4$ alkylthiocarbamoyl.

Examples of alkyl at $R^5$ are those mentioned above. Preferred is alkyl having 1 to 8 carbon atoms, particularly alkyl having 1 to 5 carbon atoms.

Alkylene at D and D' is that having 1 to 10 carbon atoms, such as methylene, ethylene, propylene, trimethylene, tetramethylene, pentamethylene, hexamethylene, heptamethylene, octamethylene, nonamethylene and decamethylene, which may have branched chain. Alkylene having substituent is that having substituent such as hydroxy, hydroxyalkyl (e.g. hydroxymethyl, 2-hydroxyethyl, 3-hydroxypropyl, particularly hydroxy $C_1$–$C_4$ alkyl), alkoxycarbonyl (e.g. methoxycarbonyl, ethoxycarbonyl, propoxycarbonyl, butoxycarbonyl, particularly $C_1$–$C_4$ alkoxycarbonyl), carboxyl, carbamoyl, or mono- or dialkylcarbamoyl (e.g. methylcarbamoyl, dimethylcarbamoyl, ethylcarbamoyl, diethylcarbamoyl, propylcarbamoyl, dipropylcarbamoyl, particularly mono- or di-$C_1$–$C_4$ alkylcarbamoyl), at an optional position of alkylene, which is exemplified by 2-hydroxytrimethylene, 1-hydroxymethylethylene, 2-carboxyethylene, 2-ethoxycarbonylethylene, 4-ethoxycarbonyltetramethylene, 2-carbamoylethylene, 2-N-methylcarbamoylethylene, 2-N-ethylcarbamoylethylene and 2-N,N-dimethylcarbamoylethylene. Alkylene having oxo is, for example, —CH$_2$CO—, —CH$_2$CH$_2$CO—, —CH$_2$CH$_2$CH$_2$CO— or —CH$_2$CH$_2$CH$_2$CH$_2$CO—.

Alkoxyalkyl at E and E' is methoxymethyl, ethoxymethyl, propoxymethyl, isopropoxymethyl, butoxymethyl, isobutoxymethyl, tert-butoxymethyl, pentyloxymethyl, hexyloxymethyl, octyloxymethyl, decyloxymethyl, dodecyloxymethyl, octadecyloxymethyl, icosyloxymethyl, 2-methoxyethyl, 3-methoxypropyl, 3-propoxypropyl, 4-methoxybutyl or 4-isopropoxybutyl, particularly $C_1$–$C_{20}$ alkoxy $C_1$–$C_4$ alkyl.

With regard to $R^6$ and $R^7$, alkyl is that having 1 to 20 carbon atoms, such as methyl, ethyl, propyl, isopropyl, butyl, isobutyl, tert-butyl, pentyl, hexyl, octyl, decyl, dodecyl, octadecyl and icosyl and cycloalkyl is that having 3 to 7 carbon atoms, such as cyclopropyl, cyclobutyl, cyclopentyl, cyclohexyl and cycloheptyl. Acyl is alkanoyl having 1 to 5 carbon atoms, such as acetyl, propionyl, isopropionyl, butyryl, pivaloyl and valeryl, or benzoyl. Alkoxycarbonyl is alkoxycarbonyl having 2 to 21 carbon atoms, such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, octyloxycarbonyl, decyloxycarbonyl, dodecyloxycarbonyl, octadecyloxycarbonyl and icosyloxycarbonyl, mono- or dialkylcarbamoyl is carbamoyl substituted by alkyl at its nitrogen atom, which is exemplified by N-methylcarbamoyl, N,N-dimethylcarbamoyl, N-ethylcarbamoyl, N,N-diethylcarbamoyl, N-propylcarbamoyl, N,N-dipropylcarbamoyl, N-isopropylcarbamoyl and N-butylcarbamoyl, particularly mono- or di-$C_1$–$C_4$ alkylcarbamoyl. Mono- or dialkylthiocarbamoyl is thiocarbamoyl substituted by alkyl at its nitrogen atom, which is exemplified by N-methylthiocarbamoyl, N,N-dimethylthiocarbamoyl, N-ethylthiocarbamoyl, N,N-diethylthiocarbamoyl, N-propylthiocarbamoyl, N,N-dipropylthiocarbamoyl, N-isopropylthiocarbamoyl and N-butylthiocarbamoyl, particularly mono- or di-$C_1$–$C_4$ alkylthiocarbamoyl. Hydroxyalkyl is that having 1 to 5 carbon atoms, such as hydroxymethyl, 1-hydroxyethyl, 2-hydroxyethyl, 2-hydroxypropyl, 3-hydroxypropyl, 2,3-dihydroxypropyl, 4-hydroxybutyl and 5-hydroxypentyl. Alkoxycarbonylalkyl is methoxycarbonylmethyl, ethoxycarbonylmethyl, propoxycarbonylethyl, isopropoxycarbonylethyl, butoxycarbonylmethyl, isobutoxycarbonylethyl, tert-butoxycarbonylmethyl, pentyloxycarbonylmethyl, hexyloxycarbonylmethyl, octyloxycarbonylmethyl, decyloxycarbonylethyl, dodecyloxycarbonylmethyl, octadecyloxycarbonylmethyl or icosyloxycarbonylmethyl, particularly $C_1$–$C_{20}$ alkoxycarbonyl $C_1$–$C_4$ alkyl. Carboxyalkyl is that having 2 to 5 carbon atoms, such as carboxymethyl, 2-carboxyethyl, 3-carboxypropyl and 4-carboxybutyl. Phenylalkylcarbamoyl is benzylcarbamoyl, 2-phenylethylcarbamoyl or 3-phenylpropylcarbamoyl, particularly phenyl $C_1$–$C_4$ alkylcarbamoyl. Phenylalkylthiocarbamoyl is benzylthiocarbamoyl, 2-phenylethylthiocarbamoyl or 3-phenylpropylthiocarbamoyl, particularly phenyl $C_1$–$C_4$ alkylthiocarbamoyl. Phenylalkyl is phenyl-substituted alkyl having 1 to 8 carbon atoms, such as benzyl, 1-phenylethyl, 2-phenylethyl, 3-phenylpropyl, 4-phenylbutyl, 6-phenylhexyl and 8-phenyloctyl. Heteroarylalkyl is alkyl having 1 to 4 carbon atoms which is substituted by heteroaryl such as furyl, thienyl, pyridyl and pyrimidinyl and is exemplified by 2-thenyl, 3-thenyl, furfuryl, 3-furylmethyl, 2-, 3- or 4-pyridylmethyl and 2-pyrimidinylmethyl. The substituents for the optionally substituted phenyl, phenylcarbamoyl, phenylthiocarbamoyl, phenylalkylcarbamoyl, phenylalkylthiocarbamoyl, phenylalkyl and heteroarylalkyl are, for example, 1 to 3 groups selected from halogen (e.g. chlorine, fluorine, bromine, iodine), alkyl (e.g. $C_1$–$C_4$ alkyl such as methyl, ethyl, propyl, isopropyl, butyl, isobutyl and tert-butyl), alkoxy (e.g. $C_1$–$C_4$ alkoxy such as methoxy, ethoxy, propoxy, isopropoxy, butoxy, isobutoxy and tert-butoxy), haloalkyl (e.g. halo $C_1$–$C_4$ alkyl such as trifluoromethyl and 2,2,2-trifluoroethyl), hydroxy, nitro and amino.

Optionally condensed heterocyclic ring formed by $R^6$ and $R^7$ together with the adjoining nitrogen atom is, for example, 1-pyrrolidinyl, piperidino, 1-piperazinyl, 4-alkyl-1-piperazinyl, 4-phenyl-1-piperazinyl, 4-substituted phenyl-1-piperazinyl, 4-aralkyl-1-piperazinyl, 4-substituted aralkyl-1-piperazinyl, 4-acyl-1-piperazinyl, 4-alkyl-1-homopiperazinyl, 4-acyl-1homopiperazinyl, morpholino, thiomorpholino, 2-oxo-1-pyrrolidinyl, 2,4-dioxo-1-pyrrolidinyl, 2-oxo-1-piperidinyl, isoindolin-2-yl, 1,2,3,4-tetrahydroquinolin-1-yl or 1,2,3,4-tetrahydroisoquinolin-2-yl. The morpholino and thiomorpholino may be substituted by carboxyl, hydroxyalkyl (e.g. hydroxymethyl, 2-hydroxyethyl, 3-hydroxypropyl), aminoalkyl (e.g. aminomethyl, 2-aminoethyl), mono- or dialkylaminoalkyl (e.g. methylaminomethyl, dimethylaminomethyl, 2-dimethylaminoethyl), alkoxycarbonyl (e.g. methoxycarbonyl, ethoxycarbonyl, propoxycarbonyl, isopropoxycarbonyl, butoxycarbonyl), carboxyalkoxyalkyl (e.g. carboxymethoxymethyl, 2-carboxyethoxymethyl, 3-carboxypropoxymethyl), alkoxycarbonylalkoxyalkyl (e.g. methoxycarbonylmethoxymethyl, ethoxycarbonylmethoxymethyl, 2-ethoxycarbonylethoxymethyl, 3-ethoxycarbonylpropoxymethyl), carboxyalkylaminoalkyl (e.g. carboxymethylaminomethyl, 2-carboxyethylaminomethyl, 3-carboxypropylaminomethyl), mono- or dihydroxyalkylamino (e.g. hydroxymethylamino, 2-hydroxyethylamino, 2,3-dihydroxypropylamino), or mono- or dialkoxyalkylamino (e.g. methoxymethylamino, ethoxymethylamino, 2-ethoxyethylamino, 2,3-diethoxypropylamino). Alkyl which substitutes the 4-position of piperazine is, for example, methyl, ethyl, propyl, isopropyl or butyl; acyl is, for example, acetyl, propionyl or butyryl; aralkyl is, for example, benzyl, 2-phenylethyl or 3-phenylpropyl; and the substituents for phenyl and aralkyl are exemplified by halogen, alkyl and alkoxy. Also, the isoindoline ring and the 1,2,3,4-tetrahydro(iso)quinoline ring may be substituted by 1 to 3 substituents optionally selected from halogen, alkyl, alkoxy, haloalkyl, hydroxyl, nitro, amino and oxo.

Examples of the heterocyclic ring which $R^6$ and $R^7$ form together with the adjoining nitrogen atom include the following.

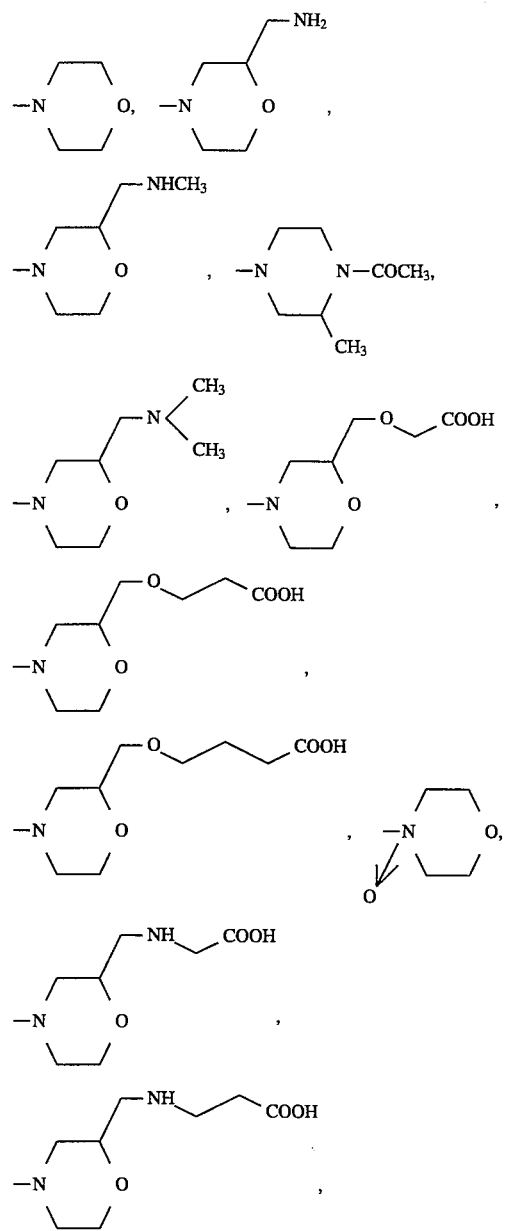

-continued

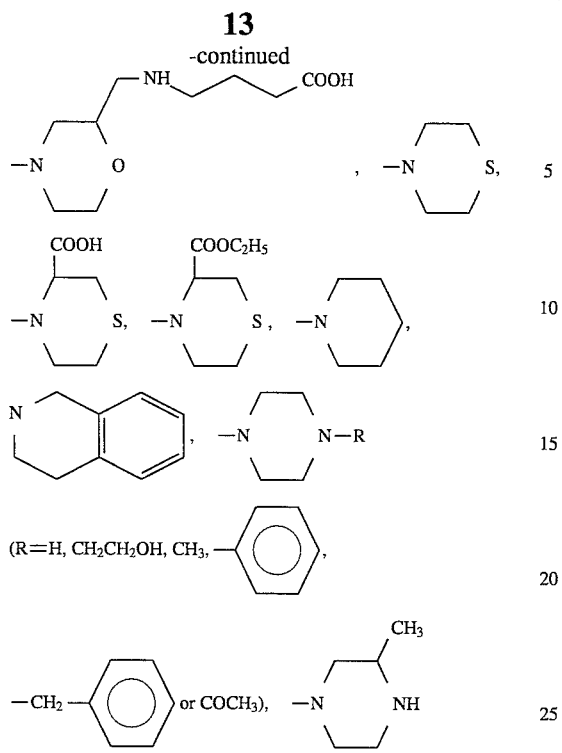

wherein alkyl, acyl, carboxyalkyl and optionally substituted phenyl alkyl at $R^8$ are as defined above.

The group of the formula (b) is exemplified by the following.

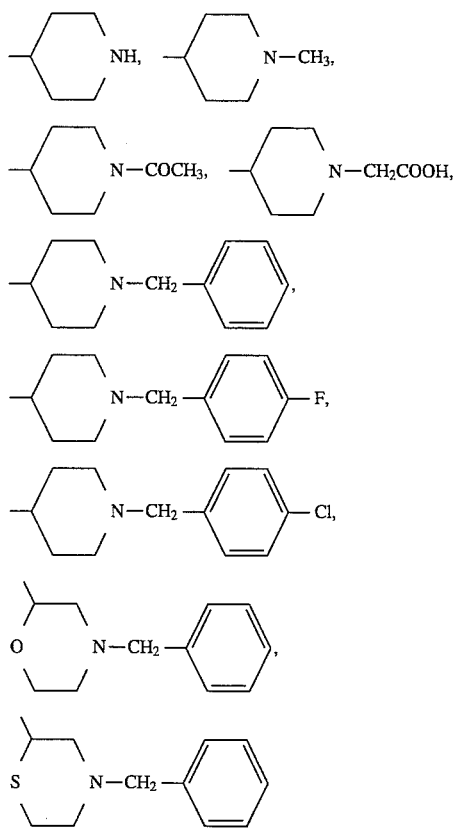

Preferable groups for E are as follows.

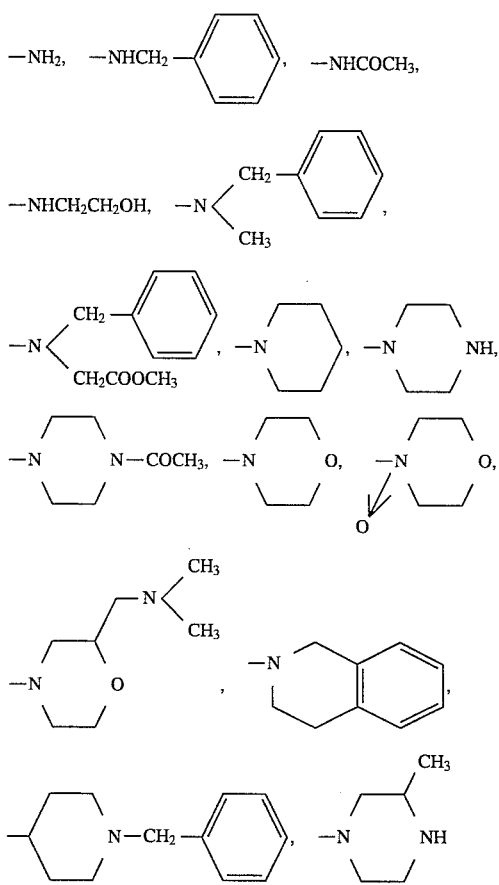

Examples of alkyl at E are those mentioned for alkyl at $R^5$.

Examples of halogen, alkyl, alkoxy, alkoxycarbonyl and haloalkyl at $R^{1'}$ are those mentioned for those at $R^1$.

Examples of alkoxycarbonyl, hydroxyalkyl and acyloxyalkyl at $R^{4'}$ are those those mentioned for those at $R^4$.

Examples of halogen at $R^{1a}$ and $R^{1b}$ are those mentioned above. Examples of alkyl having respective carbon atoms at $R^{1a}$, $R^{2a}$, $R^{3a}$, $R^{5a}$ and $R^{5b}$ are those mentioned above having corresponding carbon atoms and examples of alkoxy having respective carbon atoms at $R^{1a}$ and $R^{1b}$ are those mentioned above having corresponding carbon atoms.

While the compound of the formula (I) of the present invention comprises various isomers, the present invention encompasses an isomer or a mixture of isomers.

The pharmaceutically acceptable salt of the compound of the formula (I) includes acid addition salts such as hydrochloride, hydrobromide, hydroiodide, sulfate, nitrate, phosphate, acetate, citrate, maleate, fumarate, malonate, malate, tartrate, succinate, methanesulfonate, benzenesulfonate and a salt of the formula

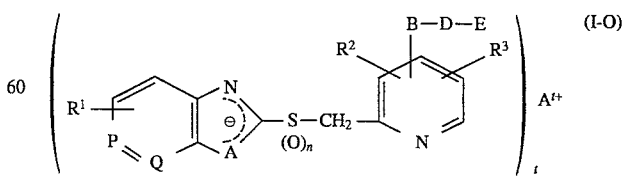

wherein t is 1, 2 or 4, $A^{t+}$ is $Li^+$, $Na^+$, $K^+$, $Mg^{2+}$, $Ca^{2+}$, $Ti^{4+}$ or $N^+(R)_4$ wherein R is alkyl having 1 to 4 carbon atoms and other symbols are as defined above. In the compounds of the formula (I-0), sodium salt, potassium salt and magnesium salt are particularly preferable. The compound of the present invention may exist as hydrates (e.g. semi-hydrate, mono-hydrate, sesqui-hydrate) or solvates, which are also encompassed in the present invention.

The compounds of the formula (I) can be produced by the following methods.

Method 1: A compound of the formula (II)

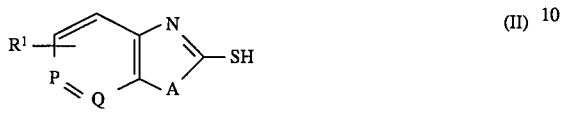

wherein each symbol is as defined above, is reacted with a compound of the formula (III)

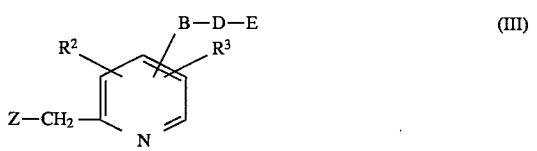

wherein Z is a reactive atom or group such as halogen or sulfonyloxy group (e.g. methanesulfonyloxy, benzenesulfonyloxy, p-toluenesulfonyloxy) and other symbols are as defined above, or an acid addition salt thereof to give a compound of the formula (I-1)

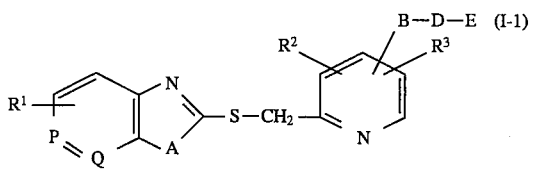

wherein each symbol is as defined above. A compound of the formula (I) wherein n is 1 or 2 can be obtained by subjecting a compound of the formula (I-1) wherein n is 0 to oxidation.

The reaction between a Compound (II) and a Compound (III) generally proceeds in a solvent inert to the reaction, such as water, methanol, ethanol, dimethylformamide and a mixed solvent thereof, preferably aqueous ethanol, in the presence of a base such as sodium hydroxide, potassium hydroxide, sodium hydride, potassium hydride, sodium methoxide, sodium carbonate, potassium carbonate, metallic sodium, triethylamine and pyridine at a temperature of from about 0° C. to the boiling point of the solvent used, preferably from 20° C. to 80° C. for about 10 minutes to 24 hours, preferably 30 minutes to 7 hours.

Examples of the acid addition salt of Compound (III) include hydrochloride and hydrobromide.

Examples of the oxidizing agent to be used for the oxidation include meta-chloroperbenzoic acid, peracetic acid, trifluoroperacetic acid, permaleic acid, potassium hyperoxide, sodium bromite, sodium hypobromite and hydrogen peroxide. The reaction is generally carried out in a solvent inert to the reaction such as water, dichloromethane, chloroform, tetrahydrofuran, dioxane, dimethylformamide and a mixed solvent thereof in the presence of an organic acid such as formic acid, acetic acid, propionic acid, butyric acid, maleic acid, fumaric acid, malonic acid, succinic acid, benzoic acid, metachlorobenzoic acid, p-nitrobenzoic acid and phthalic acid at a temperature of from −70° C. to the boiling point of the solvent used, generally from −50° C. to room temperature, preferably from −20° C. to 0° C. for about 5 minutes to 24 hours, preferably about 5 minutes to 20 hours, or in water or an alcohol solvent such as ethanol, methanol and propanol, in the presence of an alkali such as alkali hydroxide (e.g. sodium hydroxide, potassium hydroxide, calcium hydroxide) at a temperature of from −70° C. to the boiling point of the solvent used, generally from −50° C. to room temperature, preferably from −20° C. to 10° C. for about 5 minutes to 24 hours, preferably about 1 hour to 10 hours.

Method 2: A compound of the formula (I-2)

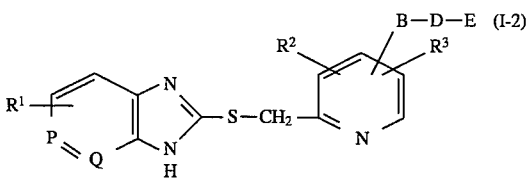

wherein each symbol is as defined above, is reacted with a compound of the formula (IV)

$$R^9\text{—NCX} \qquad (IV)$$

wherein $R^9$ is sodium, potassium or alkyl and X is oxygen atom or sulfur atom, or a compound of the formula (V)

wherein $R^{10}$ and $R^{11}$ are alkyl, Hal is halogen and X is as defined above, in a suitable solvent such as acetic acid, tetrahydrofuran and acetonitrile to give a compound of the formula (I) wherein $R^4$ is carbamoyl, mono- or dialkylcarbamoyl, thiocarbamoyl or mono- or dialkylthiocarbamoyl and n is 0.

Method 3: A compound of the formula (I-2) is reacted with alkoxycarbonyl halide, haloalkyl alcohol, alkoxyhaloalkyl, acyloxyhaloalkyl, alkyl, haloalkyl ester, haloalkylcarnoxylic acid, carbamoylhaloalkyl, or mono- or di-alkylcarbamoylhaloalkyl in the presence of an acid scavenger to give a compound of the formula (I) wherein $R^4$ is alkoxycarbonyl, hydroxyalkyl, alkoxyalkyl, acyloxyalkyl, alkoxycarbonylalkyl, carboxyalykl, carbamoylalkyl or mono- or dialkylcarbamoylalkyl and n is 0.

Examples of acid scavenger include sodium hydride, sodium hydroxide, potassium hydroxide, sodium methylate, potassium carbonate and metallic sodium.

The reaction generally proceeds in a solvent inert to the reaction, such as N,N-dimethylformamide, ethanol, methanol, chloroform and water, at −20°–140° C., preferably 0°–80° C. for about 10 minutes to 24 hours, preferably for 30 minutes to 6 hours.

Method 4: A compound of the formula (I-3)

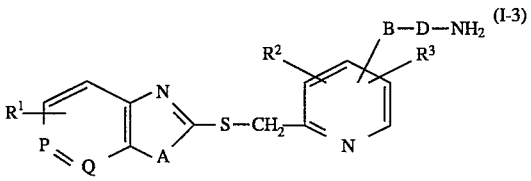

wherein each symbol is as defined above, is reacted with a compound of the formula (VII) or a compound of the formula (VI)

wherein $R^{12}$ and $R^{13}$ are the same or different and each is hydrogen, alkyl, optionally substituted phenyl or optionally substituted phenylalkyl and Hal and X are as defined above, in a suitable solvent such as acetic acid, tetrahydrofuran and acetonitrile to give a compound of the formula (I) wherein $R^6$ and $R^7$ of E (a) are carbamoyl, mono- or dialkylcarbamoyl, optionally substituted phenylcarbamoyl, -thiocarbamoyl, mono- or dialkylthiocarbamoyl, optionally substituted phenylthiocarbamoyl, optionally substituted phenylalkylcarbamoyl or optionally substituted phenylalkyl thiocarbamoyl.

Method 5: A compound of the formula (I-4)

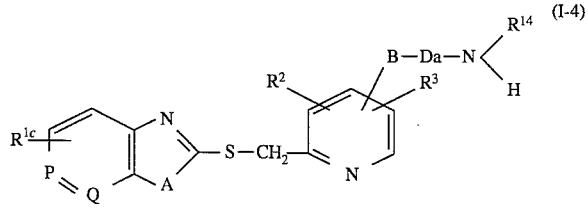

wherein $R^{1c}$ is hydrogen, halogen, alkyl, alkoxy, carboxyl, haloalkyl or nitro, Da is alkylene or alkylene substituted by carboxyl, $R^{14}$ is hydrogen, acyl or alkoxycarbonyl and other symbols are as defined above, is reacted with a compound of the formula (VII)

wherein $R^{15}$ is alkyl, cycloalkyl, hydroxyalkyl, carboxyalkyl, optionally substituted phenylalkyl or optionally substituted heteroarylalkyl and Hal is as defined above, in a solvent inert to the reaction such as alcohol (e.g. methanol, ethanol), acetonitrile, tetrahydrofuran, benzene, toluene, dimethylformamide and a mixed solvent thereof, in the presence of an acid scavenger such as potassium carbonate, sodium carbonate, sodium methylate, sodium ethylate, sodium hydroxide, potassium tert-butoxide or triethylamine to give a compound of the formula (I-5)

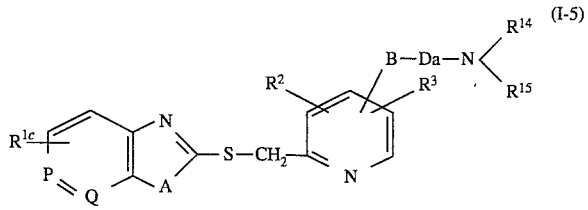

wherein each symbol is as defined above.

A compound of the formula (I-6)

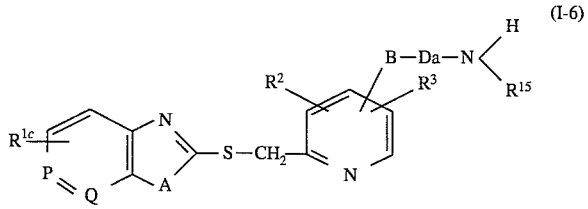

wherein each symbol is as defined above, can be obtained by hydrolyzing the compound of the formula (I-5) with an acid or alkali.

Further, a compound of the formula (I-7)

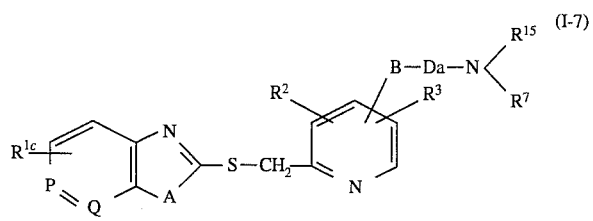

wherein each symbol is as defined above, can be obtained by reacting a compound of the formula (I-6) with a compound of the formula (VIII)

wherein each symbol is as defined above, in a solvent inert to the reaction, in the presence of an acid scavenger.

Method 6: A corresponding compound of the formula (I-1) having a carboxylic acid can be obtained by hydrolyzing a compound of the formula (I-1) having ester at the substituent $R^1$, A, D or E, with an acid or alkali.

The compound (I) thus obtained can be isolated and purified by a conventional method such as recrystallization and column chromatography.

The optical isomer of the compound (I) of the present invention can be produced by subjecting a reaction product to fractional crystallization or conducting the above-mentioned reactions using a starting compound optically resolved in advance.

The compound of the formula (I) of the present invention can be converted to the aforementioned acid addition salt by treating with hydrochloric acid, hydrobromic acid, hydroiodic acid, sulfuric acid, nitric acid, phosphoric acid, acetic acid, citric acid, maleic acid, fumaric acid, malonic acid, malic acid, tartaric acid, succinic acid, methanesulfonic acid or benzenesulfonic acid by a conventional method. Moreover, the compound of the formula (I') can be obtained by reacting with the corresponding salt.

The compound of the formula (III) can be produced, for example, by the following reactions.

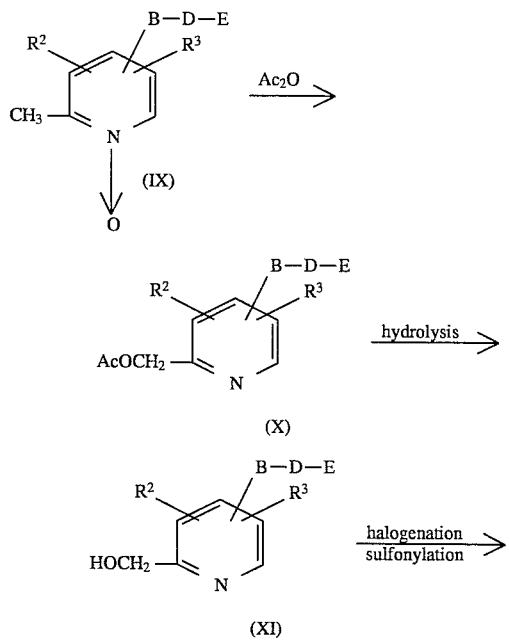

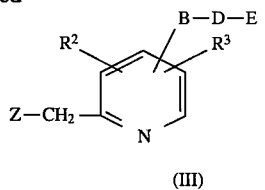

(III)

wherein Ac is acetyl and other symbols are as defined above.

That is, a compound of the formula (IX) is heated with acetic anhydride to give a compound of the formula (X), which is hydrolyzed using sodium hydroxide or the like and treated with a halogenating agent such as thionyl chloride or with a sulfonylating agent such as methanesulfonyl chloride, whereby a compound of the formula (III) is produced.

A compound of the formula (IX) can be produced by the following reactions.

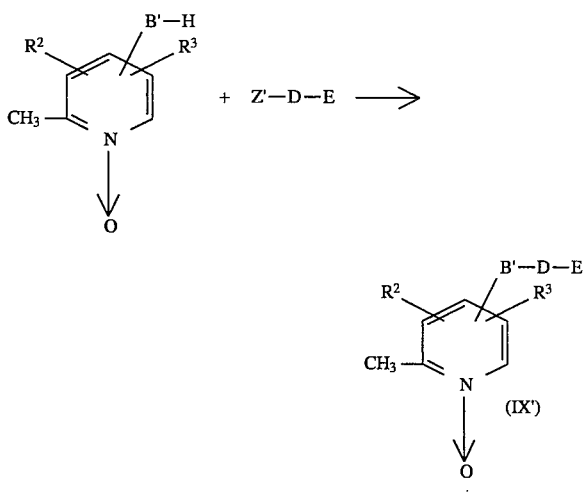

wherein B' is a sulfur atom, Z' is a leaving group such as chlorine, bromine, iodine, methanesulfonyloxy and p-toluenesulfonyloxy and other symbols are as defined above,

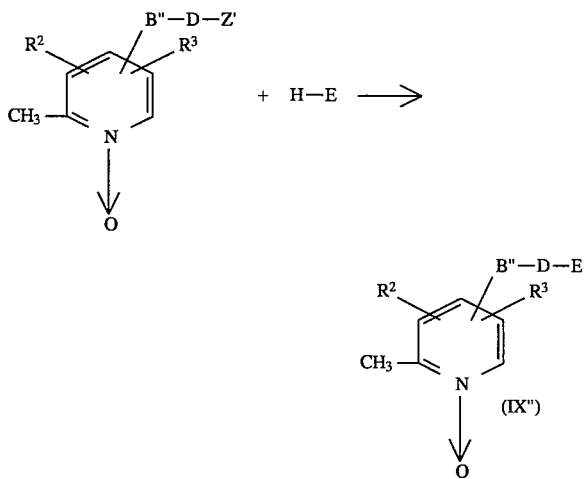

wherein B" is a sulfur atom and other symbols are as defined above, and

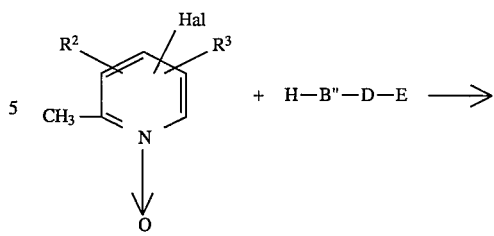

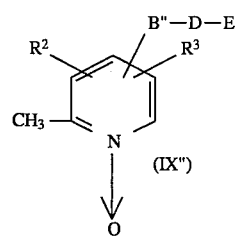

wherein each symbol is as defined above.

The above-mentioned reactions proceed in a solvent inert to the reaction, such as water, alcohol (e.g. methanol, ethanol), chloroform, dichloromethane, benzene, toluene, dimethylformamide and a mixed solvent thereof, in the presence of a base such as sodium hydroxide, potassium hydroxide, sodium hydride, sodium methoxide, sodium ethoxide, sodium carbonate, potassium carbonate, metallic sodium, triethylamine and pyridine at a temperature of from about 0° C. to the boiling point of the solvent used, preferably from 20° C. to 80° C. for about 10 minutes to 24 hours, preferably for 30 minutes to 7 hours.

The compound of the formula (IX) wherein B is SO or $SO_2$ can be produced by subjecting a compound of the formula (IX) wherein B is a sulfur atom to oxidation. The oxidizing agent to be used for the oxidation includes, for example, metachloroperbenzoic acid, peracetic acid, trifluoroperacetic acid, permaleic acid, potassium hyperoxide, sodium bromite, sodium hypobromite and hydrogen peroxide. The reaction is carried out in a solvent inert to the reaction, such as water, dichloromethane, chloroform, tetrahydrofuran, dioxane, dimethylformamide and a mixed solvent thereof, in the presence of an organic acid such as formic acid, acetic acid, propionic acid, butyric acid, maleic acid, fumaric acid, malonic acid, succinic acid, benzoic acid, metachlorobenzoic acid, p-nitrobenzoic acid and phthalic acid, at a temperature of from −70° C. to the boiling point of the solvent used, generally from −50° C. to the room temperature, preferably from −20° C. to 0° C. for about 5 minutes to 24 hours, preferably for about 5 minutes to 20 hours, or in water or an alcohol solvent such as ethanol, methanol and propanol, in the presence of an alkali such as alkali hydroxide (e.g. sodium hydroxide, potassium hydroxide, calcium hydroxide) at a temperature of from −70° C. to the boiling point of the solvent used, generally from −50° C. to the room temperature, preferably from −20° C. to 10° C. for about 5 minutes to 24 hours, preferably for 1 hour to 10 hours.

In the formula (IX), the compounds wherein D is $(L-O)_q$ and L is vinylene can be produced by, for example, the following reaction scheme.

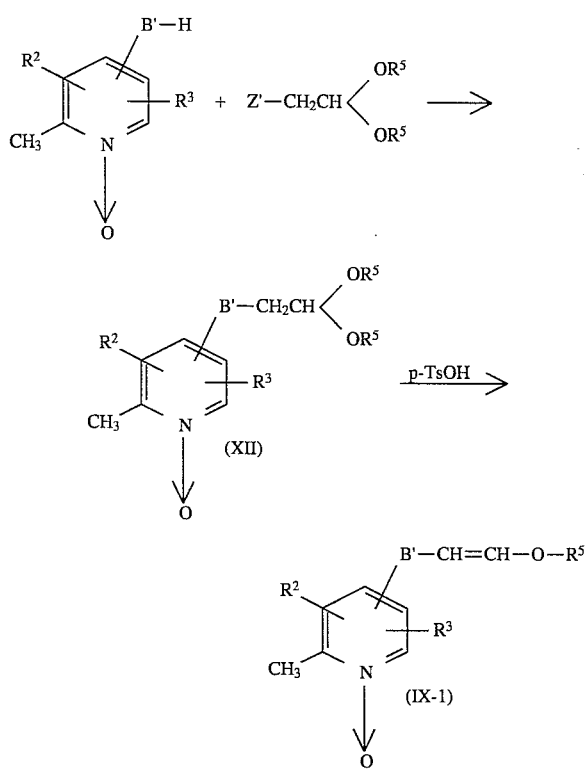

wherein each symbol is as defined above.

In the reactions as shown above, the first reaction is generally carried out in a solvent inert to the reaction, such as water, alcohol (e.g. methanol, ethanol), chloroform, dichloromethane, benzene, toluene, dimethylformamide and a mixed solvent thereof, in the presence of a base such as sodium hydroxide, potassium hydroxide, sodium hydride, sodium methoxide, sodium ethoxide, sodium carbonate, potassium carbonate, metallic sodium, triethylamine and pyridine at a temperature of from about 0° C. to the boiling point of the solvent used, preferably 20–80° C. for about 10 minutes to 24 hours, preferably for 30 minutes to 7 hours. The compound of the formula (XII) is reacted in a solvent insoluble in water, such as benzene and toluene, in the presence of an acid such as p-toluenesulfonic acid (p-TsOH) at a temperature of from about 0° C. to the boiling point of the solvent used, preferably at the boiling point of the solvent used for about 30 minutes to 48 hours, preferably for 3 hours to 12 hours to give a compound of (IX-1).

The compound of the formula (II) can be produced by, for example, the following reaction scheme.

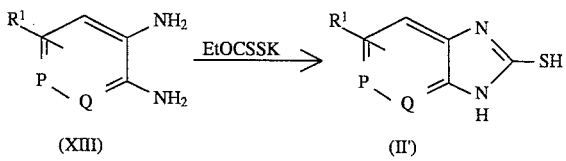

wherein each symbol is as defined above.

That is, a compound of the formula (XIII) and potassium xanthate are reacted in a solvent inert to the reaction, such as water, methanol and ethanol, at a temperature of from 0° C. to the boiling point of the solvent used, preferably from 30° C. to 80° C. for about 10 minutes to 24 hours, preferably for 1 hour to 5 hours to give a compound of the formula (II) wherein A is NH [i.e., compound of the formula (II')].

The compounds of the present invention show selective antibacterial activity against the bacteria belonging to the genus Helicobacter represented by *Helicobacter pylori* and are useful for the prevention and treatment of various diseases caused by Helicobacter. That is, the Compounds (I) of the present invention are usable for mammals inclusive of human for the prevention and treatment of various diseases caused by the bacteria belonging to the genus Helicobacter, the prevention of recurrence and relapse of ulcer, suppression of vomiting, the prevention and treatment of non-ulcer dyspepsia and the prevention and treatment of ulcer, carcinoma of stomach and the like. In addition, the Compounds (I) of the present invention have antiulcer activity, gastric acid secretion-suppressive activity, gastrointestinal cytoprotective activity and anti-diarrhea activity and are useful for the prevention and treatment of gastrointestinal diseases such as gastric ulcer, duodenal ulcer, gastritis, diarrhea and colitis. The compounds of the present invention have low toxicity, are stable to acid etc. and show small increase in gastrin value in blood. Such pharmacological action of the Compounds (I) of the present invention can be confirmed by the method of Ghosh et al, Br. J. Pharmacol. 13, p 54 (1958).

Experimental Example 1

Antibacterial activity (in vitro) of the compound of the present invention against *Helicobacter pylori* was determined by the following agar plate dilution method.

Clinical isolates (18 strains) were inoculated on Brucella agar supplemented with 5% horse serum and incubated in a microaerophilic environment at 37° C. for 72 hours. The cultures were diluted with Brucella broth to give a concentration of approximately $10^6$ cell/ml. The diluted bacterial solution was spot inoculated with a microplanter on an agar plate containing 2-fold dilution concentration series of the test compound. The cells were incubated at 37° C. under 8% $CO_2$ for 3–4 days. The minimum inhibitory concentration (MIC) in respective strains was defined as the concentration at which no more than five colonies were detected, based on which $MIC_{50}$ and $MIC_{50}$ were calculated.

The results are shown in Table 1.

TABLE 1

| Test compound (Example No.) | $MIC_{50}$ (μg/ml) | $MIC_{90}$ (μg/ml) |
|---|---|---|
| 1 | ≦0.006 | 0.012 |
| 2 | ≦0.006 | ≦0.006 |
| 3 | 0.025 | 0.05 |
| 7 | 0.012 | 0.025 |
| 12 | 0.012 | 0.025 |
| 28 | 0.025 | 0.025 |
| 1011 | 0.025 | 0.05 |
| 1012 | 0.012 | 0.025 |
| 1013 | 0.025 | 0.025 |
| Ref. Compound 1 | 0.05 | 0.10 |
| Ref. Compound 2 | 0.10 | 0.20 |
| Ref. Compound 3 | 0.05 | 0.10 |

Reference Compound 1: 2-((3-methyl-4-(2-(1,2,3,4-tetrahydroisoquinolin-2-yl)ethoxy)-2-pyridyl)methylthio)-1H-benzimidazole (Compound 16 of WO92/12976)
Reference Compound 2: 2-((3-methyl-4-(2-(N-benzyl-N-methylamino)ethoxy)-2-pyridyl)methylsulfinyl)-1H-benzimidazole ½ magnesium salt (Compound 17 of WO92/12976)
Reference Compound 3: 2-((3-methyl-4-(2-(1,2,3,4-tetrahydroisoquinolin-2-yl)ethoxy)-2-pyridyl)methylsulfinyl)-1H-benzimidazole ½ magnesium salt (Compound 20 of WO92/12976)

Experimental Example 2

The test bacterium precultured in Muller-Hinton liquid medium was diluted with the same medium to give a bacterial solution of about 106 cell/ml for inoculation. The dilute bacterial solution was spot inoculated with a microplanter on an agar plate containing 2-fold dilution concentration series of the test compound and the cells were incubated at 37° C. for 18 hours. The minimum inhibitory concentration (MIC) in respective strains was defined as the concentration at which no more than five colonies were detected. The results are shown in Table 2.

TABLE 2

| Test compound | MIC (μg/ml) | | | |
| --- | --- | --- | --- | --- |
| (Example No.) | S. aureus | E. coli | P. aeruginosa | C. albicans |
| 1 | >100 | >100 | >100 | >100 |
| 2 | >100 | >100 | >100 | >100 |
| 3 | >100 | >100 | >100 | >100 |
| 7 | >100 | >100 | >100 | >100 |
| 28 | >100 | >100 | >100 | >100 |

S. aureus: Staphylococcus aureus FDA 209P
E. coli: Escherichia coli NIHJ JC-2
P. aeruginosa: Pseudomonas aeruginosa IFO 12582
C. albicans: Candida albicans IFO 1060

As is evident from Table 2, the compound of the formula (I) was ineffective against Gram positive bacteria, Gram negative bacteria and fungi.

Experimental Example 3

Male rats weighing about 200 g (16 rats per group) were fasted for 20 hours and the test solution was orally administered to the rats. Thirty minutes later, aspirin (100 mg/kg) containing 0.3N hydrochloric acid was orally administered.

Four hours later, the stomach was removed and the area which developed ulcer was examined. A square root of the total ulcer area was taken as an ulcer index.

TABLE 3

| Test compound (Example No.) | Dose (mg/kg p.o.) | Ulcer index (mean ± standard error) | Change (%) |
| --- | --- | --- | --- |
| Control | | 5.0 ± 0.51 | |
| 1 | 10 | 3.1 ± 0.33** | −37 |
|  | 30 | 2.3 ± 0.49** | −55 |

Experimental Example 4

Action on gastric acid secretion of rats subjected to gastroperfusion

The experiment was done according to the method of Ghosh et al, Br. J. Pharmacol. 13, p 54 (1958). Wistar rats were fasted for 20 hours and anesthetized with urethane (1.5 g/kg, subcutaneous). A polyethylene tube for injection and discharge for gastroperfusion was attached to the rats. Gastroperfusion was performed using physiological saline (37° C.) at a speed of 7 ml/min and the perfusate was recovered at 10-min intervals. Histamine hydrochloride (1 mg/kg) was intravenously administered at 1-hr intervals to induce secretion of gastric acid. A test solution containing the test compound was intravenously administered 5 minutes before the histamine hydrochloride administration. The acidity of the gastric acid was titrated up to pH 7.0 with an automatic titrator and percent suppression of gastric acid secretion by the test compound was determined. The results are shown in Table 4.

TABLE 4

| Test compound (Example No.) | Dose (mg/kg i.v.) | Suppression (%) |
| --- | --- | --- |
| 1016 | 3 | 100 |

Experimental Example 5

The compound of Example 2 was orally administered to male ddY mice by 1000 mg/kg or intraperitoneally by 300 mg/kg and the mice were observed for 5 days. As a result, no death case was found.

When the compound of the present invention is used as a pharmaceutical preparation, a therapeutically effective amount of Compound (I) or a pharmaceutically acceptable salt thereof is admixed with pharmaceutically acceptable additives such as excipients, carriers, diluents and solubilizers and formulated into capsules, tablets (inclusive of sugar-coated tablets and film-coated tablets), granules, injections or infusions for administration. The dose is generally about 0.01–30 mg/kg, preferably 0.1–3 mg/kg daily for an adult by oral administration, though it is subject to change depending on the symptom, age, resistance to drug etc. of the patients.

BEST MODE FOR EMBODYING THE INVENTION

The present invention is explained in more detail by illustrating Reference Examples and Examples, to which the invention is not limited.

Reference Example 1

4-(2-Chloroethylthio)-2,3-dimethylpyridine-N-oxide (6 g) was dissolved in a mixed solution of dimethylformamide-toluene (1:1) and thereto were added potassium carbonate (4.3 g), potassium iodide (4.4 g) and morpholine (1.9 ml). The mixture was reacted at 50–55° C. for 12 hours. After the completion of the reaction, inorganic matters were filtered off and the solvent was distilled away. Water was added to the residue and the mixture was extracted with chloroform. After drying over anhydrous magnesium sulfate, the chloroform was distilled away and the obtained residue was purified by silica gel column chromatography to give 3.4 g of 2,3-dimethyl-4-(2-morpholinoethylthio)pyridine-N-oxide.

$^1$H-NMR (CDCl$_3$): 2.34 (s,3H), 2.55 (s,3H), 2.44–2.60 (m,4H), 2.71 (t,2H), 3.09 (t,2H), 3.64–3.80 (m,4H), 6.96 (d, 1H), 8.07 (d,1H)

Reference Example 2

2,3-Dimethyl-4-(2-(1,2,3,4-tetrahydroisoquinolin-2-yl) ethylthio)pyridine-N-oxide $^1$H-NMR (CDCl$_3$): 2.32 (s,3H), 2.52 (s,3H), 2.70–3.00 and 3.08–3.29 (m,8H), 3.70 (s,2H), 7.00 (d,1H), 7.02–7.20 (m,4H), 8.05 (d,1H) cl Reference Example 3

4-(2-(N-Benzyl-N-methylamino)ethylthio)-2,3-dimethylpyridine-N-oxide $^1$H-NMR (CDCl$_3$): 2.28 (s,3H), 2.31 (s,3H), 2.53 (s,3H), 2.70 (t,2H), 3.04 (t,2H), 3.58 (s,2H), 6.76 (d,1H), 7.26 (s,5H), 7.93 (d,1H)

Reference Example 4

2,3-Dimethyl-4-(2-piperidinoethylthio)pyridine-N-oxide

Reference Example 5

2,3-Dimethyl-4-(2-morpholinoethylthio)pyridine-N-oxide (3.0 g) was dissolved in acetic anhydride (30 ml) and the mixture was stirred at 90° C. for 1.5 hours. The solvent was distilled away and water was added to the residue. The mixture was extracted with chloroform and dried over anhydrous magnesium sulfate, and the solvent was distilled away. The residual 2-acetoxymethyl-3-methyl-4-(2-morpholinoethylthio)pyridine (3.2 g) was dissolved in methanol (30 ml) and thereto was added sodium hydroxide (0.88 g) in water (10 ml) under ice-cooling. The mixture was stirred under ice-cooling for 1.5 hours and at room temperature for 2 hours. After the completion of the reaction, the methanol was distilled away and the residue was extracted with chloroform. The chloroform layer was dried over anhydrous magnesium sulfate and the solvent was distilled away to give 2.1 g of 2-hydroxymethyl-3-methyl-4-(2-morpholinoethylthio)pyridine.

$^1$H-NMR (CDCl$_3$): 2.36 (s,3H), 2.47–2.67 (m,4H), 2.75 (t,2H), 3.15 (t,2H), 3.68–3.87 (m,4H), 4.68 (s,2H), 7.05 (d,1H), 8.23 (d,1H)

The following compounds were obtained in the same manner.

Reference Example 6

2-Hydroxymethyl-3-methyl-4-(2-(1,2,3,4-tetrahydroisoquinolin-2-yl)ethylthio)pyridine

Reference Example 7

4-(2-(N-Benzyl-N-methylamino)ethylthio)-2-hydroxymethyl-3-methylpyridine $^1$H-NMR (CDCl$_3$): 2.18 (s,3H), 2.33 (s,3H), 2.81 (t,2H), 3.10 (t,2H), 3.60 (s,2H), 4.81 (s,2H), 6.92 (d,1H), 7.30 (s,5H), 8.21 (d,2H)

Reference Example 8

2-Hydroxymethyl-3-methyl-4-(2-piperidinoethylthio)pyridine

EXAMPLE 1

Thionyl chloride (20 ml) was dropwise added to 2-hydroxymethyl-3-methyl-4-(2-morpholinoethylthio)pyridine (2 g) under ice-cooling and the mixture was stirred at room temperature for 1.5 hours. After the completion of the reaction, the thionyl chloride was distilled away. The residue was alkali-oversaturated with potassium carbonate and extracted with chloroform. The chloroform layer was dried over anhydrous magnesium sulfate and the solvent was distilled away to give 2.1 g of 2-chloromethyl-3-methyl-4-(2-morpholinoethylthio)pyridine as an oily substance. The oily substance was added to ethanol (50 ml) containing a solution of 2-mercaptobenzimidazole (1.0 g) and sodium hydroxide (0.6 g) in water (10 ml) and the mixture was refluxed under heating for 5 hours. After the completion of the reaction, the ethanol was distilled away and water was added to the residue, followed by extraction with chloroform. The extract was dried over anhydrous magnesium sulfate and the solvent was distilled away. Acetone was added to the residue to allow crystallization. The obtained crystals were recrystallized from a mixed solvent of ethanol-acetone to give 2-((3-methyl-4-(2-morpholinoethylthio)-2-pyridyl)methylthio)-1H-benzimidazole as white crystals, melting point 201°–203° C.

$^1$H-NMR (CDCl$_3$): 2.37 (s,3H), 2.43–2.60 (m,4H), 2.70 (t,2H), 3.10(t,2H), 3.72 (m,4H), 4.41 (s,2H), 7.08 (d,1H), 8.29 (d,1H), 7.08–7.26 and 7.45–7.56 (m,4H)

EXAMPLE 2

Thionyl chloride (20 ml) was dropwise added to 2-hydroxymethyl-3-methyl-4-(2-(1,2,3,4-tetrahydroisoquinolin-2-yl)ethylthio)pyridine (2.8 g) under ice-cooling and the mixture was stirred at room temperature for 1.5 hours. After the completion of the reaction, the thionyl chloride was distilled away. The residue was alkali-oversaturated with potassium carbonate and extracted with chloroform. The chloroform layer was dried over anhydrous magnesium sulfate and the solvent was distilled away to give 2.1 g of 2-chloromethyl-3-methyl-4-(2-(1,2,3,4-tetrahydroisoquinolin-2-yl)ethylthio)pyridine. The product was added to ethanol (30 ml) containing a solution of 2-mercaptobenzimidazole (1.3 g) and sodium hydroxide (1.2 g) in water (10 ml) and the mixture was refluxed under heating for 2 hours. After the completion of the reaction, the ethanol was distilled away and water was added to the residue, followed by extraction with chloroform. The extract was dried over anhydrous magnesium sulfate and the solvent was distilled away. Acetone was added to the residue to allow crystallization. The obtained crystals were recrystallized from isopropyl alcohol to give 2-((3-methyl-4-(2-(1,2,3,4-tetrahydroisoquinolin-2-yl)ethylthio)-2-pyridyl)methylthio)-1H-benzimidazole as crystals, melting point 90°–94° C.

$^1$H-NMR (CDCl$_3$): 2.38 (s,3H), 2.94 (t,2H), 2.94 (s,4H), 3.26 (t,2H), 3.84 (s,2H), 4.43 (s,2H), 7.00–7.60 (m, 9H), 8.30 (d,1H)

EXAMPLE 3

Thionyl chloride (10 ml) was dropwise added to 4-(2-(N-benzyl-N-methylamino)ethylthio)-2-hydroxymethyl-3-methylpyridine (1.8 g) under ice-cooling and the mixture was stirred at room temperature for 1.5 hours. After the completion of the reaction, thionyl chloride was distilled away. The residue was alkali-oversaturated with potassium carbonate and extracted with chloroform. The chloroform layer was dried over anhydrous magnesium sulfate and the solvent was distilled away to give 1.7 g of 4-(2-(N-benzyl-N-methylamino)ethylthio)-2-chloromethyl-3-methylpyridine. The product was added to ethanol (30 ml) containing a solution of 2-mercaptobenzimidazole (0.9 g) and sodium hydroxide (0.5 g) in water (10 ml) and the mixture was refluxed under heating for 7 hours. After the completion of the reaction, the ethanol was distilled away and water was added to the residue, followed by extraction with chloroform. The extract was dried over anhydrous magnesium sulfate and the solvent was distilled away. Acetone was added to the residue to allow crystallization. The obtained crystals were recrystallized from a mixed solvent of acetone-isopropyl ether to give 2-((4-(2-(N-benzyl-N-methylamino)ethylthio)-3-methyl-2-pyridyl)methylthio)-1H-benzimidazole as crystals, melting point 110°–112° C.

$^1$H-NMR (CDCl$_3$): 2.31 (s,6H), 2.76 (t,2H), 3.10 (t,2H), 3.60 (s,2H), 4.40 (s,2H), 6.90 (d,1H), 7.10–7.58 (m,9H), 8.20 (d,1H)

EXAMPLE 4

Thionyl chloride (15 ml) was dropwise added to 2-hydroxymethyl-3-methyl-4-(2-piperidinoethylthio)pyridine (2.5 g) under ice-cooling and the mixture was stirred at room temperature for 3 hours. After the completion of the reaction, thionyl chloride was distilled away. The residue was alkali-oversaturated with potassium carbonate and extracted with chloroform. The chloroform layer was dried over anhydrous magnesium sulfate and the solvent was distilled away to give 2.0 g of 2-chloromethyl-3-methyl-4-(2-piperidinoethylthio)pyridine as an oily substance. The substance was added to ethanol (50 ml) containing a solution of 2-mercaptobenzimidazole (1.0 g) and sodium hydroxide (0.6 g) in water (10 ml) and the mixture was refluxed under heating for 5 hours. After the completion of the reaction, the ethanol was distilled away and water was added to the residue, followed by extraction with chloroform. The extract was dried over anhydrous magnesium sulfate and the solvent was distilled away. The residue was recrystallized to give 2-((3-methyl-4-(2-piperidinoethylthio)-2-pyridyl)methylthio)-1H-benzimidazole, melting point 138°–140° C.

EXAMPLE 5

The same reaction as in Example 1 was carried out using 4-(2-(2-dimethylaminomethylmorpholino)ethylthio)-2-hydroxymethyl-3-methylpyridine in place of 2-hydroxymethyl-3-methyl-4-(2-morpholinoethylthio)pyridine to give 2-((4-(2-(2-dimethylaminomethylmorpholino)ethylthio)-3-methyl-2-pyridyl)methylthio)-1H-benzimidazole.

$^1$H-NMR (CDCl$_3$): 1.72–2.88 (m,8H), 2.26 (s,6H), 2.35 (s,3H), 3.09 (t,2H), 3.50–4.00 (m,3H), 4.44 (s,2H), 7.00–7.28 and 7.30–7.60 (m,5H), 8.20 (d,1H)

EXAMPLE 6

The same reaction as in Example 1 was carried out using 2-hydroxymethyl-3-methyl-4-(2-(2-dimethylaminomethylmorpholino)-2-oxoethylthio)pyridine in place of 2-hydroxymethyl-3-methyl-4-(2-morpholinoethylthio)pyridine to give 2-((3-methyl-4-(2-(2-dimethylaminomethylmorpholino)-2-oxoethylthio)-2-pyridyl)methylthio)-1H-benzimidazole 3/2 hydrate, melting point 160° C.

EXAMPLE 7

The same reaction as in Example 1 was carried out using 4-(1-benzyl-4-piperidyl)thio-2-hydroxymethyl-3-methylpyridine in place of 2-hydroxymethyl-3-methyl-4-(2-morpholinoethylthio)pyridine, followed by treatment with ethanolic hydrochloric acid to give 2-((4-(1-benzyl-4-piperidyl)thio-3-methyl-2-pyridyl)methylthio)-1H-benzimidazole hydrochloride hydrate, melting point 168° C. (dec.).

EXAMPLE 8

The same reaction as in Example 1 was carried out using 4-(2-(4-acetylpiperazin-1-yl)ethylthio)-2-hydroxymethyl-3-methylpyridine in place of 2-hydroxymethyl-3-methyl-4-(2-morpholinoethylthio)pyridine to give 2-((3-methyl-4-(2-(4-acetylpiperazin-1-yl)ethylthio)-2-pyridyl)methylthio)-1H-benzimidazole ½ hydrate, melting point 129°–131° C.

EXAMPLE 9

The same reaction as in Example 1 was carried out using 2-hydroxymethyl-3-methyl-4-(2-acetylaminoethylthio)pyridine in place of 2-hydroxymethyl-3-methyl-4-(2-morpholinoethylthio)pyridine to give 2-((3-methyl-4-(2-acetylaminoethylthio)-2-pyridyl)methylthio)-1H-benzimidazole 1/4 ethanol, melting point 211°–213° C.

EXAMPLE 10

The same reaction as in Example 1 was carried out using 2-hydroxymethyl-3-methyl-4-(3-morpholinopropylthio)pyridine in place of 2-hydroxymethyl-3-methyl-4-(2-morpholinoethylthio)pyridine to give 2-((3-methyl-4-(3-morpholinopropylthio)-2-pyridyl)methylthio)-1H-benzimidazole as crystals, melting point 149°–150° C.

EXAMPLE 11

The same reaction as in Example 1 was carried out using 2-mercaptobenzothiazole in place of 2-mercaptobenzimidazole to give 2-((3-methyl-4-(2-morpholinoethylthio)-2-pyridyl)methylthio)benzothiazole as crystals, melting point 91°–93° C.

EXAMPLE 12

The same reaction as in Example 1 was carried out using 2-hydroxymethyl-3-methyl-4-(2-(1,2,3,4-tetrahydroisoquinolin-2-yl)ethylthio)pyridine in place of 2-hydroxymethyl-3-methyl-4-(2-morpholinoethylthio)pyridine and 2-mercaptoimidazo[5,4-b]pyridine in place of 2-mercaptobenzimidazole to give 2-((3-methyl-4-(2-(1,2,3,4-tetrahydroisoquinolin-2-yl)ethylthio)-2-pyridyl)methylthio)imidazo[5,4-b]pyridine as crystals, melting point 180° C.

EXAMPLE 13

The same reaction as in Example 1 was carried out using 2-hydroxymethyl-3-methyl-4-(2-(1,2,3,4-tetrahydroisoquinolin-2-yl)ethylthio)pyridine in place of 2-hydroxymethyl-3-methyl-4-(2-morpholinoethylthio)pyridine and 2-mercaptoimidazo[5,4-c]pyridine in place of 2-mercaptobenzimidazole to give 2-((3-methyl-4-(2-(1,2,3,4-tetrahydroisoquinolin-2-yl)ethylthio)-2-pyridyl)methylthio)imidazo[5,4-c]pyridine as crystals, melting point 215° C. (dec.).

EXAMPLE 14

The same reaction as in Example 1 was carried out using 2-hydroxymethyl-4-(2-(1,2,3,4-tetrahydroisoquinolin-2-yl)ethylthio)pyridine in place of 2-hydroxymethyl-3-methyl-4-(2-morpholinoethylthio)pyridine to give 2-((4-(2-(1,2,3,4-tetrahydroisoquinolin-2-yl)ethylthio)-2-pyridyl)methylthio)-1H-benzimidazole as crystals, melting point 125°–127° C.

EXAMPLE 15

2-((3-Methyl-4-(2-(4-acetylpiperazin1-yl)ethylthio)-2-pyridyl)methylthio)-1H-benzimidazole (38 g) was dissolved in 6N hydrochloric acid and the mixture was stirred at 50° C. for 2 hours. After the completion of the reaction, the mixture was made alkaline with potassium carbonate and extracted with a mixed solvent of chloroform-methanol. The chloroform-methanol layer was dried over anhydrous magnesium sulfate, the solvent was distilled away and the residue was recrystallized from ethanol to give 2-((3-methyl-4-(2-(piperazin1-yl)ethylthio)-2-pyridyl)methylthio)-1H-benzimidazole as crystals, melting point 166°–168° C.

EXAMPLE 16

The same reaction as in Example 15 was carried out using 2-((3-methyl-4-(2-acetylaminoethylthio)-2-pyridyl)methylthio)-1H-benzimidazole in place of 2-((3-methyl-4-(2-(4-acetylpiperazin-1-yl)ethylthio)-2-pyridyl)methylthio)-1H-benzimidazole to give 2-((3-methyl-4-(2-aminoethylthio)-2- pyridyl)methylthio)-1H-benzimidazole 1/5 hydrate, melting point 158°–160° C.

EXAMPLE 17

2-((3-Methyl-4-(2-morpholinoethylthio)-2-pyridyl)methylthio)-1H-benzimidazole (10 g) was reacted with 1.1 equivalents of ethyl chlorocarbonate in dimethylformamide in the presence of 1.1 equivalents of sodium hydride at room temperature. After the completion of the reaction, the solvent was distilled away and water was added to the residue, followed by extraction with chloroform. The chloroform layer was dried over anhydrous magnesium sulfate and the solvent was distilled away to give 11 g of ethyl 2-((3-methyl-4-(2-morpholinoethylthio)-2-pyridyl)methylthio)-1H-benzimidazole1-carboxylate as crystals, melting point 145°–147° C.

EXAMPLE 18

The same reaction as in Example 17 was carried out using chloroacetic acid in place of ethyl chlorocarbonate to give 2-((3-methyl-4-(2-morpholinoethylthio)-2-pyridyl)methylthio)-1H-benzimidazole-1-acetic acid as crystals, melting point 223°–225° C.

EXAMPLE 19

The same reaction as in Example 17 was carried out using methyl chlorocarbonate in place of ethyl chlorocarbonate to give methyl 2-((3-methyl-4-(2-morpholinoethylthio)-2-pyridyl)methylthio)-1H-benzimidazole-1-carboxylate as crystals, melting point 151°–153° C.

EXAMPLE 20

The same reaction as in Example 17 was carried out using ethylene bromohydrin in place of ethyl chlorocarbonate to give 2-(2-((3-methyl-4-(2-morpholinoethylthio)-2-pyridyl)methylthio)-1H-benzimidazol-1-yl)ethanol as crystals, melting point 41°–143° C.

EXAMPLE 21

The same reaction as in Example 17 was carried out using methyl chloroacetate in place of ethyl chlorocarbonate to give methyl 2-((3-methyl-4-(2-morpholinoethylthio)-2-pyridyl)methylthio)-1H-benzimidazole1-acetate as crystals, melting point 128°–129° C.

EXAMPLE 22

The same reaction as in Example 17 was carried out using dimethylcarbamyl chloride in place of ethyl chlorocarbonate to give N,N-dimethyl-2-((3-methyl-4-(2-morpholinoethylthio)-2-pyridyl)methylthio)-1H-benzimidazole1-acetamide as crystals, melting point 178°–180° C.

EXAMPLE 23

The same reaction as in Example 17 was carried out using dimethylcarbamylmethyl chloride in place of ethyl chlorocarbonate to give 1-(N,N-dimethylcarbamoyl)-2-((3-methyl4-(2-morpholinoethylthio)-2-pyridyl)methylthio)-1H-benzimidazole ¼ hydrate as crystals, melting point 117°–119° C.

EXAMPLE 24

The same reaction as in Example 17 was carried out using methyl iodide in place of ethyl chlorocarbonate, followed by treatment with ethanolic hydrochloric acid to give 1-methyl-2-((3-methyl-4-(2-morpholinoethylthio)-2-pyridyl)methylthio)-1H-benzimidazole hydrochloride 1/5 hydrate as crystals, melting point 214°–216° C.

EXAMPLE 25

The same reaction as in Example 17 was carried out using 2-chloroacetamide in place of ethyl chlorocarbonate to give 2-((3-methyl-4-(2-morpholinoethylthio)-2-pyridyl)methylthio)-1H-benzimidazole-1-acetamide 1/5 hydrate as crystals, melting point 178°–180° C.

EXAMPLE 26

The same reaction as in Example 17 was carried out except that 2-((3-methyl-4-(2-(1,2,3,4-tetrahydroisoquinolin-2-yl)ethylthio)-2-pyridyl)methylthio)-1H-benzimidazole was reacted with ethyl chlorocarbonate, in place of 2-((3-methyl-4-(2-morpholinoethylthio)-2-pyridyl)methylthio)-1H-benzimidazole, to give ethyl 2-((3-methyl-4-(2-(1,2,3,4-tetrahydroisoquinolin-2-yl)ethylthio)-2-pyridyl)methylthio)-1H-benzimidazole-1-carboxylate 1/2 ·ethanol as crystals, melting point 134°–136° C. (dec.).

EXAMPLE 27

2-Hydroxymethyl-3-methyl-4-(2-morpholinoethylthio)pyridine (6.2 g) was dissolved in chloroform and thereto was dropwise added thionyl chloride (2 ml) under ice-cooling. The mixture was stirred at room temperature for 1 hour. After the completion of the reaction, the reaction mixture was poured into ice-water and made alkaline with potassium carbonate, followed by extraction with chloroform. The chloroform layer was dried over anhydrous magnesium sulfate and the solvent was distilled away to give 6.0 g of 2-chloromethyl-3-methyl-4-(2-morpholinoethylthio)pyridine as an oily substance. The substance was added to ethanol (60 ml) containing a solution of 5-methoxycarbonyl-2-mercaptobenzimidazole (5.1 g) and sodium hydroxide (1.6 g) in water (10 ml) and the mixture was refluxed under heating for 3.5 hours. After the completion of the reaction, the ethanol was distilled away and the residue was dissolved in water. The aqueous layer was washed with chloroform and dilute hydrochloric acid was dropwise added until crystals precipitated in the aqueous layer. The resultant crystals were collected by filtration to give 2-((3-methyl-4-(2-morpholinoethylthio)-2-pyridyl)methylthio)-1H-benzimidazole-5-carboxylic acid 7/2 hydrate, melting point 120–124° C.

EXAMPLE 28

2-((3-Methyl-4-(2-morpholinoethylthio)-2-pyridyl)methylthio)-1H-benzimidazole (3 g) was dissolved in chloroform and thereto was added meta-chloroperbenzoic acid (1.9 g) at −50° C. The mixture was stirred at −30° C. for 5 hours. After the completion of the reaction, an aqueous solution of sodium thiosulfate was added thereto and the mixture was stirred. The chloroform layer was partitioned and dried over anhydrous magnesium sulfate. The chloroform was distilled away. The residue was purified by column chromatography to give 4-(2-((2-(1H-benzimidazol-2-yl)thiomethyl-3-methyl-4-pyridyl)thio)ethyl)morpholine N-oxide 1/2 hydrate as crystals, melting point 141°–143° C.

EXAMPLE 29

2-((3-Methyl-4-(2-aminoethylthio)-2-pyridyl)methylthio)-1H-benzimidazole (8.5 g) was dissolved in ethanol and thereto was added benzaldehyde (2.8 g). The mixture was stirred at 50°–55° C. for 5 hours and sodium borohydride (0.98 g) was added thereto under ice-cooling. The mixture was stirred at room temperature for 2 hours. After the completion of the reaction, ethanol was distilled away and the residue was eluted with chloroform. The chloroform layer was dried over anhydrous magnesium sulfate and the solvent was distilled away. The residue was purified by column chromatography to give 2-((3-methyl-4-(2-benzylaminoethylthio)-2-pyridyl)methylthio)-1H-benzimidazole.

$^1$H-NMR (CDCl$_3$): 2.33 (s,3H), 3.00 (m,4H), 3.80 (s,2H), 4.40 (s,2H), 7.00 and 8.18 (d,2H), 7.05–7.51 (m,9H)

EXAMPLE 30

2-((3-Methyl-4-(2-benzylaminoethylthio)pyridin-2-yl)methylthio)-1H-benzimidazole (2 g) was dissolved in dimethylformamide and reacted with methyl chloroacetate (0.45 ml) in the presence of potassium carbonate (0.71 g) at 50°–60° C. After the completion of the reaction, the dimethylformamide was distilled away and the residue was extracted with ethyl acetate. The ethyl acetate layer was dried over anhydrous magnesium sulfate and the solvent was distilled away to give an oily product. The oily product was purified by column chromatography to give 2-((3-methyl-4-(2-(N-benzyl-N-methoxycarbonylmethylamino)ethylthio)-2-pyridyl)methylthio)-1H-benzimidazole.

EXAMPLE 31

2-((3-Methyl-4-(2-benzylaminoethylthio)-2-pyridyl)methylthio)-1H-benzimidazole (1.88 g) was dissolved in dimethylformamide (20 ml) and thereto were added ethyl bromoacetate (0.784 g) and potassium carbonate (0.925 g). The mixture was stirred at 40°–50° C. for 1 hour. The reaction mixture was poured into water and extracted with ethyl acetate. The extract was washed with water, dried and concentrated under reduced pressure. The residue was subjected to column chromatography and eluted with chloroform-methanol to give 2-((3-methyl-4-(2-(N-benzyl-N-ethoxycarbonylmethyl)aminoethylthio)-2-pyridyl)methylthio)-1H-benzimidazole as pale yellow crystals.

The compounds of Examples 32–40 can be synthesized using 2-((3-methyl-4-(2-benzylaminoethylthio)-2-pyridyl)methylthio)-1H-benzimidazole as a starting compound.

EXAMPLE 32

2-((3-Methyl-4-(2-(N-benzyl-N-ethoxycarbonylamino)ethylthio)-2-pyridyl)methylthio)-1H-benzimidazole

EXAMPLE 33

2-((3-Methyl-4-(2-(N-benzyl-N-(2-ethoxycarbonylethyl)amino)ethylthio)-2-pyridyl)methylthio)-1H-benzimidazole

EXAMPLE 34

2-((3-Methyl-4-(2-(N-benzyl-N-(3-ethoxycarbonylpropyl)amino)ethylthio)-2-pyridyl)methylthio)-1H-benzimidazole

EXAMPLE 35

2-((3-Methyl-4-(2-(N-benzyl-N-(4-ethoxycarbonylbutyl)amino)ethylthio)-2-pyridyl)methylthio)-1H-benzimidazole

EXAMPLE 36

2-((3-Methyl-4-(2-(N-benzyl-N-(5-ethoxycarbonylpentyl)-amino)ethylthio)-2-pyridyl)methylthio)-1H-benzimidazole

EXAMPLE 37

2-((3-Methyl-4-(2-(N-benzyl-N-(2-hydroxyethyl)amino)ethylthio)-2-pyridyl)methylthio)-1H-benzimidazole

EXAMPLE 38

2-((3-Methyl-4-(2-(N-benzyl-N-(3-hydroxypropyl)amino)ethylthio)-2-pyridyl)methylthio)-1H-benzimidazole

EXAMPLE 39

2-((3-Methyl-4-(2-(N-benzyl-N-(4-hydroxybutyl)amino)ethylthio)-2-pyridyl)methylthio)-1H-benzimidazole

EXAMPLE 40

2-((3-Methyl-4-(3-(N-benzyl-N-(2,3-dihydroxypropyl)amino)ethylthio)-2-pyridyl)methylthio)-1H-benzimidazole

EXAMPLE 41

2-((3-Methyl-4-(3-benzylaminopropylthio)-2-pyridyl)methylthio)-1H-benzimidazole (2.0 g) was dissolved in dimethylformamide (25 ml) and thereto were added ethyl bromoacetate (0.834 g) and potassium carbonate (0.984 g). The mixture was stirred at 40°–50° C. for 1 hour. The reaction mixture was poured into water and extracted with ethyl acetate. The extract was washed with water, dried and concentrated under reduced pressure. The residue was subjected to column chromatography and eluted with chloroform-methanol to give 2-((3-methyl-4-(3-(N-benzyl-N-ethoxycarbonylmethylamino)propylthio)-2-pyridyl)methylthio)-1H-benzimidazole.

The compounds of Examples 42–50 can be synthesized using 2-((3-methyl-4-(3-benzylaminopropylthio)-2-pyridyl)methylthio)-1H-benzimidazole as a starting compound.

EXAMPLE 42

2-((3-Methyl-4-(3-(N-benzyl-N-ethoxycarbonylamino)propylthio)-2-pyridyl)methylthio)-1H-benzimidazole

EXAMPLE 43

2-((3-Methyl-4-(3-(N-benzyl-N-(2-ethoxycarbonylethyl)amino)propylthio)-2-pyridyl)methylthio)-1H-benzimidazole

EXAMPLE 44

2-((3-Methyl-4-(3-(N-benzyl-N-(3-ethoxycarbonylpropyl)amino)propylthio)-2-pyridyl)methylthio)-1H-benzimidazole

EXAMPLE 45

2-((3-Methyl-4-(3-(N-benzyl-N-(4-ethoxycarbonylbutyl)amino)propylthio)-2-pyridyl)methylthio)-1H-benzimidazole

EXAMPLE 46

2-(3-Methyl-4-(3-(N-benzyl-N-(5-ethoxycarbonylpentyl)amino)propylthio)-2-pyridyl)methylthio)-1H-benzimidazole

EXAMPLE 47

2-((3-Methyl-4-(3-(N-benzyl-N-(2-hydroxyethyl)amino)propylthio)-2-pyridyl)methylthio)-1H-benzimidazole

EXAMPLE 48

2-((3-Methyl-4-(3-(N-benzyl-N-(3-hydroxypropyl)amino)propylthio)-1H-benzimidazole

EXAMPLE 49

2-((3-Methyl-4-(3-(N-benzyl-N-(4-hydroxybutyl)amino)propylthio)-2-pyridyl)methylthio)-1H-benzimidazole

EXAMPLE 50

2-((3-Methyl-4-(3-(N-benzyl-N-(2,3-dihydroxypropyl)amino)propylthio)-2-pyridyl)methylthio)-1H-benzimidazole

EXAMPLE 51

2-((3-Methyl-4-(2-aminoethylthio)-2-pyridyl)methylthio)-1H-benzimidazole (2.0 g) was dissolved in dimethylformamide (20 ml) and thereto were added ethylene bromohydrin (0.83 g) and potassium carbonate (1.25 g). The mixture was stirred at 60°–70° C. for 2 hours. The reaction mixture was poured into water and extracted with ethyl acetate. The extract was washed with water, dried over anhydrous magnesium sulfate and the solvent was distilled away under reduced pressure. The residue was subjected to column chromatography and eluted with chloroform-methanol. Ethanol-hydrochloric acid was added thereto. Recrystallization from ethanol-methanol gave 2-((3-methyl-4-(2-(2-hydroxyethylamino)ethylthio)-2-pyridyl)methylthio)-1H-benzimidazole trihydrochloride hydrate as colorless crystals, melting point 215°–217° C. (dec.).

The compounds of Examples 52–54 can be synthesized using 2-((3-methyl-4-(2-aminoethylthio)-2-pyridyl)methylthio)-1H-benzimidazole as a starting compound.

EXAMPLE 52

2-((3-Methyl-4-(2-(3-hydroxypropylamino)ethylthio)-2-pyridyl)methylthio)-1H-benzimidazole

EXAMPLE 53

2-((3-Methyl-4-(2-(ethoxycarbonylmethylamino)ethylthio)-2-pyridyl)methylthio)-1H-benzimidazole dihydrochloride, melting point 233°–234° C. (dec.)

EXAMPLE 54

2-((3-Methyl-4-(2-(ethoxycarbonylamino)ethylthio)-2-pyridyl)methylthio)-1H-benzimidazole

EXAMPLE 55

2-((3-Methyl-4-(3-aminopropylthio)-2-pyridyl)methylthio)1H-benzimidazole (2.0 g) was dissolved in dimethylformamide (20 ml) and thereto were added ethylene bromohydrin (0.83 g) and potassium carbonate (1.25 g). The mixture was stirred at 60°–70° C. for 2 hours. The reaction mixture was poured into water and extracted with ethyl acetate. The extract was dried over anhydrous magnesium sulfate and the solvent was distilled away under reduced pressure. The residue was subjected to column chromatography and extracted with chloroform-methanol to give 2-((3-methyl-4-(3-(2-hydroxyethylamino)propylthio)-2-pyridyl)methylthio)-1H-benzimidazole.

The compounds of Examples 56–58 can be synthesized using 2-((3-methyl-4-(3-aminopropylthio)-2-pyridyl)methylthio)-1H-benzimidazole as a starting compound.

EXAMPLE 56

2-((3-Methyl-4-(3-(3-hydroxypropylamino)propylthio)-2-pyridyl)methylthio)-1H-benzimidazole

EXAMPLE 57

2-((3-Methyl-4-(3-(2,3-dihydroxypropylamino)propylthio)-2-pyridyl)methylthio)-1H-benzimidazole

EXAMPLE 58

2-((3-Methyl-4-(3-(ethoxycarbonylmethylamino)propylthio)-2-pyridyl)methylthio)-1H-benzimidazole

EXAMPLE 59

2-((3-Methyl-4-(2-aminoethylthio)-2-pyridyl)methylthio)-1H-benzimidazole (2.0 g) was dissolved in dimethylformamide (20 ml) and thereto were added ethylene bromohydrin (1.59 g) and potassium carbonate (2.1 g). The mixture was stirred at 70°–80° C. for 3 hours. The reaction mixture was poured into water and extracted with ethyl acetate. The extract was washed with water, dried over anhydrous magnesium sulfate and the solvent was distilled away under reduced pressure. The residue was subjected to column chromatography and eluted with chloroform-methanol to give 2-((3-methyl-4-(2-(N,N-bis(2-hydroxyethyl)amino)ethylthio)-2-pyridyl)methylthio)-1H-benzimidazole as a pale yellow oil.

The compounds of Examples 60–65 can be synthesized using 2-((3-methyl-4-(2-aminoethylthio)-2-pyridyl)methylthio)-1H-benzimidazole as a starting compound.

EXAMPLE 60

2-((3-Methyl-4-(2-(N,N-bis(ethoxycarbonylmethyl)amino)ethylthio)-2-pyridyl)methylthio)-1H-benzimidazole

EXAMPLE 61

2-((3-Methyl-4-(2-(N,N-bis(3-hydroxypropyl)amino)ethylthio)-2-pyridyl)methylthio)-1H-benzimidazole

EXAMPLE 62

2-((3-Methyl-4-(2-(N,N-bis(2-ethoxycarbonylethyl)amino)ethylthio)-2-pyridyl)methylthio)-1H-benzimidazole

Example 63

2-((3-Methyl-4-(2-(N,N-bis(3-ethoxycarbonylpropyl)amino)ethylthio)-2-pyridyl)methylthio)-1H-benzimidazole

EXAMPLE 64

2-((3-Methyl-4-(2-(N,N-bis(4-ethoxycarbonylbutyl)amino)ethylthio)-2-pyridyl)methylthio)-1H-benzimidazole

EXAMPLE 65

2-((3-Methyl-4-(2-(N,N-diethoxycarbonylamino)ethylthio)-2-pyridyl)methylthio)-1H-benzimidazole

EXAMPLE 66

2-((3-Methyl-4-(3-aminopropylthio)-2-pyridyl)methylthio)-1H-benzimidazole (2.0 g) was dissolved in dimethylformamide (20 ml) and thereto were added ethylene bromohydrin (1.52 g) and potassium carbonate (2.0 g). The mixture was stirred at 70°–80° C. for 3 hours. The reaction mixture was poured into water and extracted with ethyl acetate. The extract was washed with water, dried over anhydrous magnesium sulfate and the solvent was distilled away under reduced pressure. The residue was subjected to column chromatography and eluted with chloroform-methanol to give 2-((3-methyl-4-(3-(N,N-bis(2-hydroxyethyl)amino)propylthio)-2-pyridyl)methylthio)-1H-benzimidazole as a pale yellow oil.

The compounds of Examples 67–71 can be synthesized using 2-((3-methyl-4-(3-aminopropylthio)-2-pyridyl)methylthio)-1H-benzimidazole as a starting compound.

EXAMPLE 67

2-((3-Methyl-4-(3-(N,N-bis(ethoxycarbonylmethyl)amino)propylthio)-2-pyridyl)methylthio)-1H-benzimidazole

EXAMPLE 68

2-((3-Methyl-4-(3-(N,N-bis(3-hydroxypropyl)amino)propylthio)-2-pyridyl)methylthio)-1H-benzimidazole

EXAMPLE 69

2-((3-Methyl-4-(3-(N,N-bis(2-ethoxycarbonylethyl)amino)propylthio)-2-pyridyl)methylthio)-1H-benzimidazole

EXAMPLE 70

2-((3-Methyl-4-(3-(N,N-bis(3-ethoxycarbonylpropyl)amino)propylthio)-2-pyridyl)methylthio)-1H-benzimidazole

EXAMPLE 71

2-((3-Methyl-4-(3-(N,N-bis(4-ethoxycarbonylbutyryl)amino)propylthio)-2-pyridyl)methylthio)-1H-benzimidazole

EXAMPLE 72

2-((3-Methyl-4-(3-(N,N-diethoxycarbonylamino)propylthio)-2-pyridyl)methylthio)-1H-benzimidazole

EXAMPLE 73

2-((3-Methyl-4-(2-(N-benzyl-N-ethoxycarbonylmethylamino)ethylthio)-2-pyridyl)methylthio)-1H-benzimidazole (1.0 g) was dissolved in ethanol (10 ml) and thereto was added an aqueous solution (3 ml) of 1N sodium hydroxide. The mixture was stirred at room temperature for 1 hour. The reaction mixture was concentrated under reduced pressure and adjusted to pH 4 with an aqueous solution of dilute acetic acid. The resultant crystals were collected by filtration to give 2-((3-methyl-4(2-(N-benzyl-N-carboxymethylamino)ethylthio)-2-pyridyl)methylthio)-1H-benzimidazole as colorless crystals.

The compounds of Examples 74–95 can be synthesized in the similar manner.

EXAMPLE 74

2-((3-Methyl-4-(2-(N-benzyl-N-(2-carboxyethyl)amino)ethylthio)-2-pyridyl)methylthio)-1H-benzimidazole

EXAMPLE 75

2-((3-Methyl-4-(2-(N-benzyl-N-(3-carboxypropyl)amino)ethylthio)-2-pyridyl)methylthio)-1H-benzimidazole

EXAMPLE 76

2-((3-Methyl-4-(2-(N-benzyl-N-(4-carboxybutyl)amino)ethylthio)-2-pyridyl)methylthio)-1H-benzimidazole

EXAMPLE 77

2-((3-Methyl-4-(2-(N-benzyl-N-carboxyamino)ethylthio)-2-pyridyl)methylthio)-1H-benzimidazole

EXAMPLE 78

2-((3-Methyl-4-(3-(N-benzyl-N-carboxymethylamino)propylthio)-2-pyridyl)methylthio)-1H-benzimidazole

EXAMPLE 79

2-((3-Methyl-4-(3-(N-benzyl-N-(2-carboxyethyl)amino)propylthio)-2-pyridyl)methylthio)-1H-benzimidazole

EXAMPLE 80

2-((3-Methyl-4-(3-(N-benzyl-N-(3-carboxypropyl)amino)propylthio)-2-pyridyl)methylthio)-1H-benzimidazole

EXAMPLE 81

2-((3-Methyl-4-(3-(N-benzyl-N-(4-carboxybutyl)amino)propylthio)-2-pyridyl)methylthio)-1H-benzimidazole

EXAMPLE 82

2-((3-Methyl-4-(2-(carboxymethylamino)ethylthio)-2-pyridyl)methylthio)-1H-benzimidazole, melting point 215°–216° C. (dec.)

EXAMPLE 83

2-((3-Methyl-4-(2-(2-carboxyethylamino)ethylthio)-2-pyridyl)methylthio)-1H-benzimidazole

EXAMPLE 84

2-((3-Methyl-4-(2-(3-carboxypropylamino)ethylthio)-2-pyridyl)methylthio)-1H-benzimidazole

EXAMPLE 85

2-((3-Methyl-4-(2-(4-carboxybutylamino)ethylthio)-2-pyridyl)methylthio)-1H-benzimidazole

EXAMPLE 86

2-((3-Methyl-4-(2-(N,N-dicarboxymethylamino)ethylthio)-2-pyridyl)methylthio)-1H-benzimidazole

EXAMPLE 87

2-((3-Methyl-4-(2-(N,N-bis(2-carboxyethyl)amino)ethylthio)-2-pyridyl)methylthio)-1H-benzimidazole

EXAMPLE 88

2-((3-Methyl-4-(2-(N,N-bis(3-carboxypropyl)amino)ethylthio)-2-pyridyl)methylthio)-1H-benzimidazole

EXAMPLE 89

2-((3-Methyl-4-(2-(N,N-bis(4-carboxybutyl)amino)ethylthio)-2-pyridyl)methylthio)-1H-benzimidazole

EXAMPLE 90

2-((3-Methyl-4-(2-dimethylamino-2-carboxyethyl)thio-2-pyridyl)methylthio)-1H-benzimidazole

EXAMPLE 91

2-((3-Methyl-4-(2-amino-2-carboxyethylthio)-2-pyridyl)methylthio)-1H-benzimidazole

EXAMPLE 92

2-((3-Methyl-4-(2-morpholino-2-carboxyethylthio)-2-pyridyl)methylthio)-1H-benzimidazole

EXAMPLE 93

2-((3-Methyl-4-(2-(1,2,3,4-tetrahydroisoquinolin-2-yl)-2-carboxyethylthio)-2-pyridyl)methylthio)-1H-benzimidazole

EXAMPLE 94

2-((3-Methyl-4-(2-(2-carboxymethoxymethyl)morpholinoethylthio)-2-pyridyl)methylthio)-1H-benzimidazole

EXAMPLE 95

2-((3-Methyl-4-(2-(2-carboxymethylaminomethylmorpholino)ethylthio)-2-pyridyl)methylthio)-1H-benzimidazole

EXAMPLE 96

2-Mercaptobenzimidazole (1.5 g) was dissolved in ethanol (20 ml) and thereto were added ethyl 2-dimethylamino-3-(2-chloromethyl-3-methyl-4-pyridylthio)propionate (3.16 g) and an aqueous solution (10 ml) of 1N sodium hydroxide. The mixture was stirred at 50° C. for 1 hour. The reaction mixture was concentrated under reduced pressure and water was added to the residue. The mixture was extracted with ethyl acetate. The extract was washed with water, dried over anhydrous magnesium sulfate and the solvent was distilled away under reduced pressure. The residue was subjected to column chromatography and eluted with chloroform-methanol to give 2-((3-methyl-4-(2-dimethylamino-2-ethoxycarbonylethylthio)-2-pyridyl)methylthio)-1H-benzimidazole as a pale yellow oil.

The compounds of Examples 97–101 can be synthesized in the similar manner.

EXAMPLE 97

2-((3-Methyl-4-(2-amino-2-ethoxycarbonylethylthio)-2-pyridyl)methylthio)-1H-benzimidazole

EXAMPLE 98

2-((3-Methyl-4-(2-morpholino-2-ethoxycarbonylethylthio)-2-pyridyl)methylthio)-1H-benzimidazole

EXAMPLE 99

2-((3-Methyl-4-(2-(1,2,3,4-tetrahydroisoquinolin-2-yl)-2-ethoxycarbonylethylthio)-2-pyridyl)methylthio)-1H-benzimidazole

EXAMPLE 100

2-((3-Methyl-4-(2-(2-ethoxycarbonylmethoxymethylmorpholino)ethylthio)-2-pyridyl)methylthio)-1H-benzimidazole

EXAMPLE 101

2-((3-Methyl-4-(2-(2-ethoxycarbonylmethylaminomethylmorpholino)ethythio)-2-pyridyl)methylthio)-1H-benzimidazole

EXAMPLE 102

2-((3-Methyl-4-(2-(2-amino)ethylthio)-2-pyridyl)methylthio)-1H-benzimidazole (2.0 g) was dissolved in ethanol (20 ml) and thereto was added phenyl isocyanate (0.79 ml). The mixture was stirred for 5.5 hours. The ethanol was evaporated under reduced pressure and the resultant crystals were collected by filtration to give N-phenyl-N'-(2-(2-(1H-benzimidazol-2-yl)-thiomethyl)-3-methyl-4-pyridylthio)ethylurea, melting point 208°–210° C.

The compounds as shown in the following Tables were produced in the similar manner. In Tables, each symbol means the following.

| Me: methyl | Et: ethyl | i-Pr: isopropyl |
|---|---|---|
| Bu: butyl | Ac: acetyl | |

TABLE 4

![structure: R¹-benzazole(A)-S-CH₂-pyridine(R²,R³) with B-D-E substituent]

| No | R¹ | R² | R³ | A | B | D | E | MP (°C.) |
|---|---|---|---|---|---|---|---|---|
| 201 | 5-Cl | CH₃ | H | NH | S | CH₂CH₂ | morpholino (N...O) | |
| 202 | 5-Me | CH₃ | H | NH | S | CH₂CH₂ | morpholino | |
| 203 | 5-MeO | CH₃ | H | NH | S | CH₂CH₂ | morpholino | |
| 204 | 5-OH | CH₃ | H | NH | S | CH₂CH₂ | morpholino · 3HCl | 246–250 |
| 205 | 5-COOEt | CH₃ | H | NH | S | CH₂CH₂ | morpholino | |
| 206 | 5-CF₃ | CH₃ | H | NH | S | CH₂CH₂ | morpholino | |
| 207 | 5-NO₂ | CH₃ | H | NH | S | CH₂CH₂ | morpholino | |
| 208 | 5-NH₂ | CH₃ | H | NH | S | CH₂CH₂ | morpholino | |
| 209 | 5-NHMe | CH₃ | H | NH | S | CH₂CH₂ | morpholino | |
| 210 | 5-NMe₂ | CH₃ | H | NH | S | CH₂CH₂ | morpholino | |
| 211 | 5NHCH₂COOH | CH₃ | H | NH | S | CH₂CH₂ | 1,2,3,4-tetrahydroisoquinolin-2-yl | |
| 212 | 5NHCH₂COOEt | CH₃ | H | NH | S | CH₂CH₂ | morpholino | |
| 213 | 5NHCH₂COOH | CH₃ | H | NH | S | CH₂CH₂ | morpholino | |

TABLE 4-continued

| No | R¹ | R² | R³ | A | B | D | E | MP (°C.) |
|---|---|---|---|---|---|---|---|---|
| 214 | 5-NEt₂ | CH₃ | H | NH | S | CH₂CH₂ | morpholino | |
| 217 | H | CH₃ | H | S | S | CH₂CH₂ | tetrahydroisoquinolin-2-yl | |
| 218 | H | CH₃ | H | O | S | CH₂CH₂ | morpholino | |
| 219 | H | CH₃ | H | O | S | CH₂CH₂ | tetrahydroisoquinolin-2-yl | |
| 223 | 5NH(CH₂)₂COOH | CH₃ | H | NH | S | CH₂CH₂ | morpholino | |
| 224 | 5NH(CH₂)₃COOH | CH₃ | H | NH | S | CH₂CH₂ | morpholino | |
| 225 | H | CH₃ | H | NH | S | CH₂CH₂ | 2-methylpiperazin-1-yl·NH·4HCl | 248–250 |
| 226 | 5-OH | CH₃ | H | NH | S | CH₂CH₂ | tetrahydroisoquinolin-2-yl·HBr | 153–156 |
| 227 | 5-MeO | CH₃ | H | NH | S | CH₂CH₂ | tetrahydroisoquinolin-2-yl | 136–140 |
| 228 | 5-F | CH₃ | H | NH | S | CH₂CH₂ | tetrahydroisoquinolin-2-yl·2HCl | 246–249 |
| 229 | 5-CF₃ | CH₃ | H | NH | S | CH₂CH₂ | tetrahydroisoquinolin-2-yl·2HCl | 253–254 |

TABLE 5

| No | n | R² | R³ | A | B | D | E |
|---|---|---|---|---|---|---|---|
| 301 | 1 | CH₃ | H | NH | S | CH₂CH₂ | morpholino (N—O ring) |
| 302 | 1 | CH₃ | H | NH | S | CH₂CH₂ | 1,2,3,4-tetrahydroisoquinolin-2-yl |
| 303 | 1 | CH₃ | H | NH | S | CH₂CH₂ | N(Me)CH₂-phenyl |
| 304 | 1 | CH₃ | H | NH | S | CH₂CH₂ | piperidino |
| 305 | 1 | CH₃ | H | NH | S | CH₂CH₂ | 4-phenylpiperazin-1-yl |
| 306 | 1 | CH₃ | H | NH | S | CH₂CH₂ | 4-(4-fluorobenzyl)piperazin-1-yl |
| 307 | 1 | CH₃ | H | NH | S | CH₂CH₂ | 4-(4-chlorobenzyl)piperazin-1-yl |
| 308 | 2 | CH₃ | H | NH | S | CH₂CH₂ | morpholino |
| 309 | 2 | CH₃ | H | NH | S | CH₂CH₂ | 1,2,3,4-tetrahydroisoquinolin-2-yl |
| 310 | 1 | CH₃ | H | NH | SO₂ | CH₂CH₂ | morpholino |
| 311 | 1 | CH₃ | H | NH | SO₂ | CH₂CH₂ | 1,2,3,4-tetrahydroisoquinolin-2-yl |
| 312 | 1 | CH₃ | H | NH | SO₂ | CH₂CH₂ | N(Me)CH₂-phenyl |

TABLE 5-continued
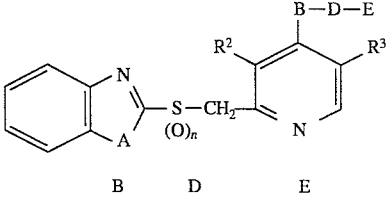
| No | n | R² | R³ | A | B | D | E |
|---|---|---|---|---|---|---|---|
| 313 | 1 | CH₃ | H | NH | SO₂ | CH₂CH₂ | 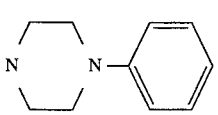 |
| 314 | 1 | CH₃ | H | NH | SO₂ | CH₂CH₂ | 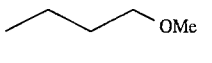 |
| 315 | 1 | CH₃ | H | NCOOMe | SO₂ | — | 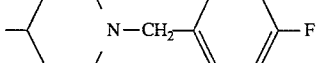 |
| 316 | 1 | CH₃ | H | NH | S | — | 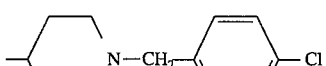 |
| 317 | 1 | CH₃ | H | NH | S | — | 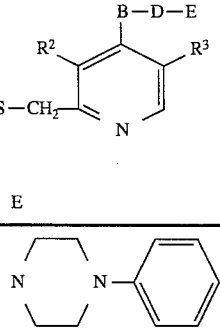 |
TABLE 6
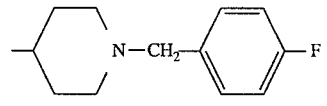
| No | R² | R³ | B | D | E | MP (°C.) |
|---|---|---|---|---|---|---|
| 401 | CH₃ | H | S | CH₂CH₂ | 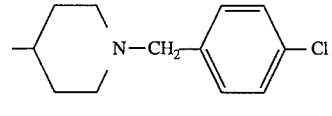 | |
| 402 | CH₃ | H | S | — | | |
| 403 | CH₃ | H | S | — | | |
| 408 | CH₃ | H | S | CH₂CH₂ | 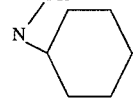 | |
| 409 | CH₃ | H | S | CH₂CH₂ | 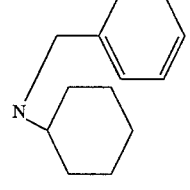 | |

TABLE 6-continued

| No | R² | R³ | B | D | E | MP (°C.) |
|---|---|---|---|---|---|---|
| 410 | CH₃ | H | S | CH₂CH₂ | N(Me)-CH₂-(2-pyridyl) | |
| 411 | CH₃ | H | S | CH₂CH₂ | N(Me)-CH₂-(3-pyridyl) | |
| 412 | CH₃ | H | S | CH₂CH₂ | N(Me)-CH₂-(4-pyridyl) | |
| 413 | CH₃ | H | S | (CH₂)₄ | morpholino | |
| 414 | CH₃ | H | S | (CH₂)₅ | morpholino | |
| 415 | CH₃ | H | S | (CH₂)₃ | 1,2,3,4-tetrahydroisoquinolin-2-yl | |
| 416 | CH₃ | H | S | (CH₂)₄ | 1,2,3,4-tetrahydroisoquinolin-2-yl | |
| 417 | CH₃ | H | S | (CH₂)₅ | 1,2,3,4-tetrahydroisoquinolin-2-yl | |
| 418 | CH₃ | H | S | CH₂CH₂ | N(Me)-phenyl | |
| 419 | CH₃ | H | S | CH₂CH₂ | N(Me)-CH₂-(4-chlorophenyl) | |
| 420 | CH₃ | H | S | CH₂CH₂ | N(Me)-CH₂-(4-methoxyphenyl) | |

TABLE 6-continued
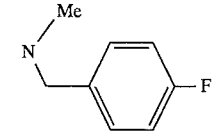
| No | R² | R³ | B | D | E | MP (°C.) |
|---|---|---|---|---|---|---|
| 421 | CH₃ | H | S | CH₂CH₂ | 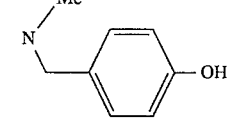 | |
| 422 | CH₃ | H | S | CH₂CH₂ | 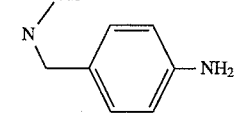 | |
| 423 | CH₃ | H | S | CH₂CH₂ |  | |
| 424 | CH₃ | H | S | (CH₂)₃ | 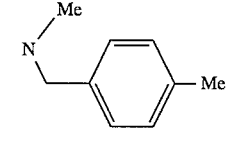 | |
| 425 | CH₃ | H | S | (CH₂)₃ | 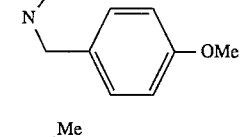 | |
| 426 | CH₃ | H | S | (CH₂)₃ | 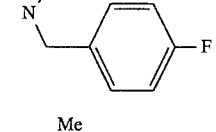 | |
| 427 | CH₃ | H | S | (CH₂)₃ | 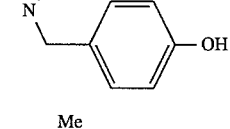 | |
| 428 | CH₃ | H | S | (CH₂)₃ | 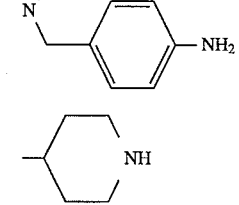 | |
| 429 | CH₃ | H | S | (CH₂)₃ |  | |
| 430 | CH₃ | H | S | — |  | |

TABLE 6-continued
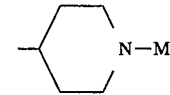
| No | R² | R³ | B | D | E | MP (°C.) |
|---|---|---|---|---|---|---|
| 431 | CH₃ | H | S | — | 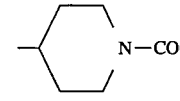 | |
| 432 | CH₃ | H | S | — | 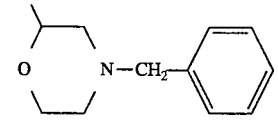 | |
| 433 | CH₃ | H | S | CH₂ | 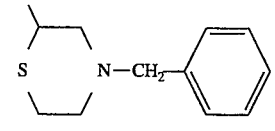 | |
| 434 | CH₃ | H | S | CH₂ | 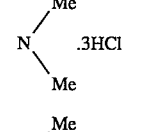 | |
| 435 | CH₃ | H | S | CH₂CH₂ | 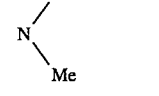  .3HCl | 216–220 |
| 436 | CH₃ | H | S | (CH₂)₃ |  | |
| 437 | CH₃ | H | S | CH₂CH₂ | NH₂ | |
| 438 | CH₃ | H | S | (CH₂)₃ | NH₂ | |
| 439 | CH₃ | H | S | CH₂CH₂ | 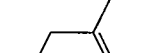 | |
| 440 | CH₃ | H | S | CH₂CH₂ | 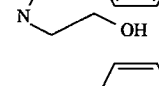 | |
| 441 | CH₃ | H | S | CH₂CH₂ | 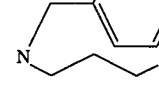 | |
| 442 | CH₃ | H | S | (CH₂)₃ | 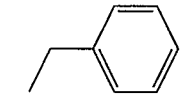 | |
| 443 | CH₃ | H | S | (CH₂)₃ | 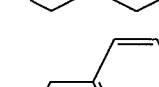 | |

TABLE 6-continued

[Structure: benzimidazole-S-CH2-pyridine with R2, R3 substituents and B-D-E group]

| No | R² | R³ | B | D | E | MP (°C.) |
|---|---|---|---|---|---|---|
| 444 | CH₃ | H | S | (CH₂)₃ | N(CH₂-phenyl)(CH₂CH₂OH) | |
| 445 | CH₃ | H | S | (CH₂)₄ | N(CH₂-phenyl)(CH₂CH₂OH) | |
| 446 | CH₃ | H | S | (CH₂)₄ | N(Me)(CH₂CH₂OH) | |
| 447 | CH₃ | H | S | (CH₂)₄ | N(CH₂-phenyl)(CH₂CH₂CH₂OH) | |
| 448 | CH₃ | H | S | CH₂CH₂ | NH-CH₂CH₂-OH | |
| 449 | CH₃ | H | S | (CH₂)₃ | NH-CH₂CH₂-OH | |
| 450 | CH₃ | H | S | CH₂CH₂ | NH-CH₂CH₂CH₂-OH | |
| 451 | CH₃ | H | S | (CH₂)₃ | NH-CH₂CH₂CH₂-OH | |
| 452 | CH₃ | H | S | CH₂CH₂ | N(CH₂CH₂OH)₂ | |
| 453 | CH₃ | H | S | (CH₂)₃ | N(CH₂CH₂OH)₂ | |
| 454 | CH₃ | H | S | CH₂CH₂ | N(CH₂CH(OH))₂ | |
| 455 | CH₃ | H | S | CH₂CH₂ | N(CH₂-phenyl)(CH₂CH(OH)CH₂OH) | |
| 456 | CH₃ | H | S | (CH₂)₃ | N(CH₂-phenyl)(CH₂CH(OH)CH₂OH) | |

TABLE 6-continued
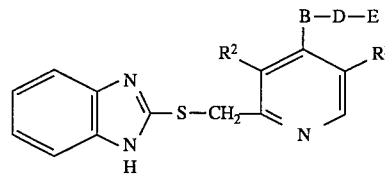
| No | R² | R³ | B | D | E | MP (°C.) |
|---|---|---|---|---|---|---|
| 457 | CH₃ | H | S | (CH₂)₃ | 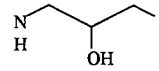 | |
| 458 | CH₃ | H | S | CH₂CH₂ | 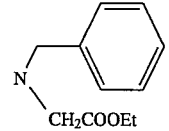 | |
| 459 | CH₃ | H | S | CH₂CH₂ | 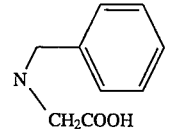 | |
| 460 | CH₃ | H | S | CH₂CH₂ | 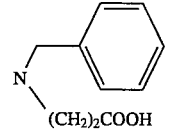 | |
| 461 | CH₃ | H | S | CH₂CH₂ | 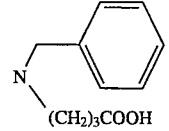 | |
| 462 | CH₃ | H | S | (CH₂)₃ | 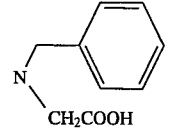 | |
| 463 | CH₃ | H | S | (CH₂)₃ | 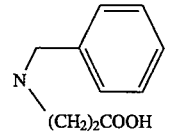 | |
| 464 | CH₃ | H | S | CH₂CH₂ | NHCSNH—Me | |
| 465 | CH₃ | H | S | CH₂CH₂ | NHCSNH—Et | |
| 466 | CH₃ | H | S | CH₂CH₂ | NHCSNH—Bu | |
| 467 | CH₃ | H | S | CH₂CH₂ | 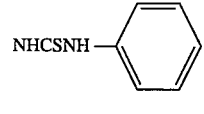 | |
| 468 | CH₃ | H | S | CH₂CH₂ | NHCONH—Me | |
| 469 | CH₃ | H | S | CH₂CH₂ | NHCONH—Et | 196–198 |
| 470 | CH₃ | H | S | CH₂CH₂ | NHCONH—Bu | 174–177 |
| 471 | CH₃ | H | S | CH₂CH₂ | 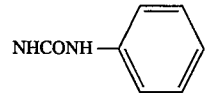 | |
| 472 | CH₃ | H | S | (CH₂)₃ | NHCSNH—Bu | |

TABLE 6-continued

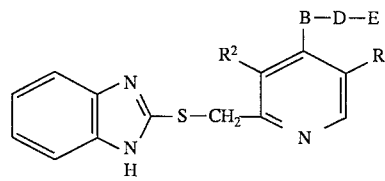

| No | R² | R³ | B | D | E | MP (°C.) |
|---|---|---|---|---|---|---|
| 473 | CH₃ | H | S | (CH₂)₃ | NHCSNH—C₆H₅ | |
| 474 | CH₃ | H | S | (CH₂)₃ | NHCONH—Bu | |
| 475 | CH₃ | H | S | (CH₂)₃ | NHCONH—C₆H₅ | |
| 476 | CH₃ | H | S | CH₂CH₂ | NH-CH₂-COOH | 215–217 |
| 477 | CH₃ | H | S | (CH₂)₃ | NH-CH₂-COOH | |
| 478 | CH₃ | H | S | CH₂CH₂ | N(CH₂COOH)₂ | |
| 479 | CH₃ | H | S | CH₂CH₂ | NH-CH₂CH₂-COOH | 217 |
| 480 | CH₃ | H | S | CH₂CH₂ | NH-CH₂CH₂CH₂-COOH | |
| 481 | CH₃ | H | S | CH(OH) with ethyl branches | NH₂ | |
| 482 | CH₃ | H | S | CH(OH) with ethyl branches | NH—Et | |
| 483 | CH₃ | H | S | CH(OH) with ethyl branches | N(i-Pr)₂ | |
| 484 | CH₃ | H | S | CH₂CH₂ | morpholinyl-CH₂-OCH₂COOH | |
| 485 | CH₃ | H | S | (CH₂)₃ | morpholinyl-CH₂-OCH₂COOH | |
| 486 | CH₃ | H | S | CH₂CH₂ | morpholinyl-CH₂-NHCH₂COOH | |

TABLE 6-continued

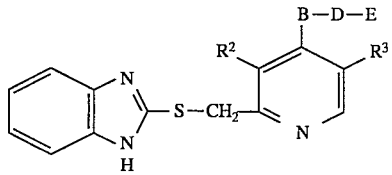

| No | R² | R³ | B | D | E | MP (°C.) |
|---|---|---|---|---|---|---|
| 487 | CH₃ | H | S | (CH₂)₃ | 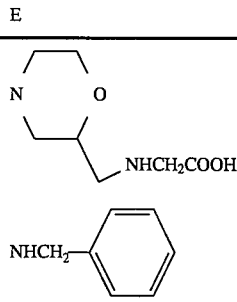 morpholine-CH₂NHCH₂COOH | |
| 488 | CH₃ | H | S | (CH₂)₃ |  NHCH₂-phenyl | |
| 489 | CH₃ | H | S | CH₂CH(CH₃) | 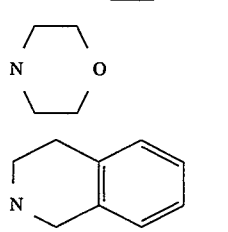 morpholine | |
| 490 | CH₃ | H | S | CH₂CH(CH₃) |  tetrahydroisoquinoline | |
| 491 | CH₃ | H | S | CH₂CH₂ | NH—Me | |
| 492 | CH₃ | H | S | CH₂CH₂ | NH—Bu | |
| 493 | CH₃ | H | S | CH₂CH(COOH) | NH₂ | |
| 494 | CH₃ | H | S | CH₂CH(COOH) | N(Me)Me | |
| 495 | CH₃ | H | S | CH₂CH(COOH) |  morpholine | |
| 496 | CH₃ | H | S | CH₂CH(COOH) |  tetrahydroisoquinoline | |
| 497 | CH₃ | H | S | CH₂CH(COOEt) | NH₂ | |
| 498 | CH₃ | H | S | CH₂CH(COOEt) | N(Me)Me | |
| 499 | CH₃ | H | S | CH₂CH(CONHMe) | NH₂ | |
| 500 | CH₃ | H | S | CH₂CH(CONHEt) | N(Me)Me | |

TABLE 6-continued

[Structure: benzimidazole-S-CH2-pyridine with R2, R3 substituents and B-D-E group at position 4]

| No | R² | R³ | B | D | E | MP (°C.) |
|---|---|---|---|---|---|---|
| 501 | CH₃ | H | S | CH₂CH₂ | tetrahydroisoquinoline-OMe | |
| 502 | CH₃ | H | S | CH₂CH₂ | tetrahydroisoquinoline-OH | |
| 503 | CH₃ | H | S | CH₂CH₂ | tetrahydroisoquinoline-Cl | |
| 504 | CH₃ | H | S | CH₂CH₂ | tetrahydroisoquinoline-Me | |
| 505 | CH₃ | H | S | CH₂CH₂ | tetrahydroisoquinoline-NH₂ | |
| 506 | CH₃ | H | S | CH₂CH₂ | tetrahydroisoquinoline-(OH)₂ .3HCl | 229–231 |
| 507 | CH₃ | H | S | CH₂CH₂ | tetrahydroisoquinoline-(OMe)₂ .HCl | 201–202 |
| 508 | CH₃ | H | S | CH₂CH₂ | tetrahydroisoquinoline-Cl₂ | |
| 509 | CH₃ | H | S | CH₂CH₂ | thiomorpholine | |
| 510 | CH₃ | H | S | CH₂CH₂ | thiomorpholine-COOEt | |
| 511 | CH₃ | H | S | CH₂CH₂ | thiomorpholine-COOH | |
| 512 | CH₃ | H | S | CH₂CH₂ | N(CH₂-C₆H₄-F)(CH₂CH₂OH) | |

TABLE 6-continued
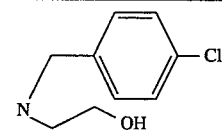
| No | R² | R³ | B | D | E | MP (°C.) |
|---|---|---|---|---|---|---|
| 513 | CH₃ | H | S | CH₂CH₂ | 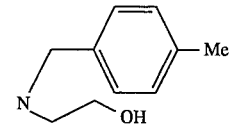 | |
| 514 | CH₃ | H | S | CH₂CH₂ | 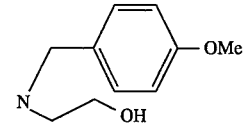 | |
| 515 | CH₃ | H | S | CH₂CH₂ | 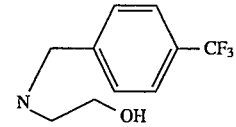 | |
| 516 | CH₃ | H | S | CH₂CH₂ | 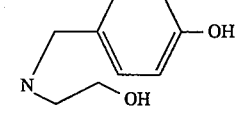 | |
| 517 | CH₃ | H | S | CH₂CH₂ | 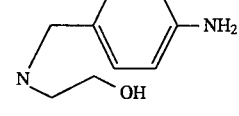 | |
| 518 | CH₃ | H | S | CH₂CH₂ | 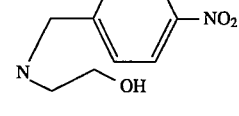 | |
| 519 | CH₃ | H | S | CH₂CH₂ | 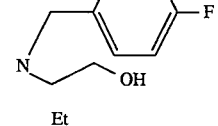 | |
| 520 | CH₃ | H | S | (CH₂)₃ | 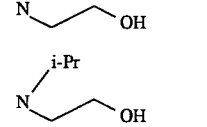 | |
| 521 | CH₃ | H | S | CH₂CH₂ | 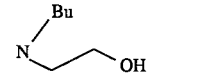 | |
| 522 | CH₃ | H | S | CH₂CH₂ | | |
| 523 | CH₃ | H | S | CH₂CH₂ |  | |

TABLE 6-continued

| No | R² | R³ | B | D | E | MP (°C.) |
|---|---|---|---|---|---|---|
| 524 | CH₃ | H | S | CH₂CH₂ | N(Me)-CH₂CH₂CH₂-OH | |
| 525 | CH₃ | H | S | CH₂CH₂ | N(Me)-(CH₂)₄-OH | |
| 526 | CH₃ | H | S | CH₂CH₂ | N(Me)-(CH₂)₅-OH | |
| 527 | CH₃ | H | S | CH₂CH₂ | N(CH₂CH₂CH₂OH)₂ | |
| 528 | CH₃ | H | S | CH₂CH₂ | N((CH₂)₄OH)₂ | |
| 529 | CH₃ | H | S | CH₂CH₂ | N((CH₂)₅OH)₂ | |
| 530 | CH₃ | H | S | CH₂CH₂ | N(CH₂-C₆H₄-4-F)(CH₂COOH) | |
| 531 | CH₃ | H | S | CH₂CH₂ | N(CH₂-C₆H₄-4-Cl)(CH₂COOH) | |
| 532 | CH₃ | H | S | CH₂CH₂ | N(CH₂-C₆H₄-4-OMe)(CH₂COOH) | |
| 533 | CH₃ | H | S | CH₂CH₂ | N(CH₂-C₆H₄-4-Me)(CH₂COOH) | |
| 534 | CH₃ | H | S | CH₂CH₂ | N(CH₂-C₆H₄-4-CF₃)(CH₂COOH) | |
| 535 | CH₃ | H | S | CH₂CH₂ | N(CH₂-C₆H₄-4-OH)(CH₂COOH) | |

TABLE 6-continued

[Structure: benzimidazole-S-CH₂-pyridine with R², R³, and B-D-E substituents]

| No | R² | R³ | B | D | E | MP (°C.) |
|---|---|---|---|---|---|---|
| 536 | CH₃ | H | S | CH₂CH₂ | 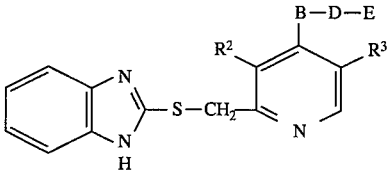 benzyl-N(CH₂COOH)- with 4-NH₂ | |
| 537 | CH₃ | H | S | CH₂CH₂ | 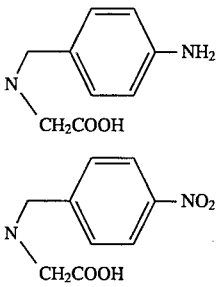 benzyl-N(CH₂COOH)- with 4-NO₂ | |
| 538 | CH₃ | H | S | CH₂CH₂ | 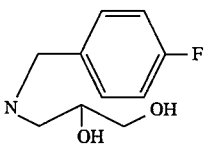 4-F-benzyl-N-CH₂CH(OH)CH₂OH | |
| 539 | CH₃ | H | S | CH₂CH₂ | 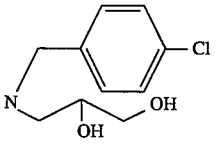 4-Cl-benzyl-N-CH₂CH(OH)CH₂OH | |
| 540 | CH₃ | H | S | (CH₂)₃ | 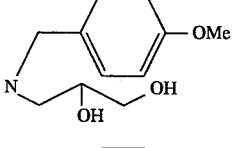 4-OMe-benzyl-N-CH₂CH(OH)CH₂OH | |
| 541 | CH₃ | H | S | CH₂CH₂ | 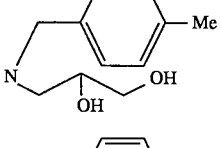 4-Me-benzyl-N-CH₂CH(OH)CH₂OH | |
| 542 | CH₃ | H | S | CH₂CH₂ | 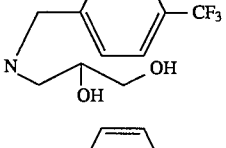 4-CF₃-benzyl-N-CH₂CH(OH)CH₂OH | |
| 543 | CH₃ | H | S | CH₂CH₂ | 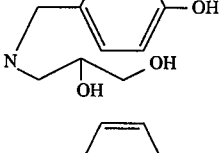 4-OH-benzyl-N-CH₂CH(OH)CH₂OH | |
| 544 | CH₃ | H | S | CH₂CH₂ | 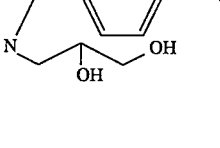 4-NH₂-benzyl-N-CH₂CH(OH)CH₂OH | |

TABLE 6-continued
| No | R² | R³ | B | D | E | MP (°C.) |
|---|---|---|---|---|---|---|
| 545 | CH₃ | H | S | CH₂CH₂ | 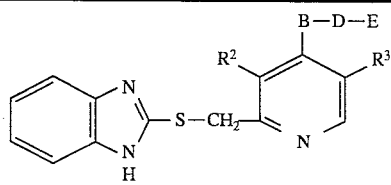 | |
| 546 | CH₃ | H | S | CH₂CH₂ | NHCONHCH₂—⟨phenyl⟩ | |
| 547 | CH₃ | H | S | CH₂CH₂ | NHCONH(CH₂)₂—⟨phenyl⟩ | |
| 548 | CH₃ | H | S | CH₂CH₂ | NHCSNHCH₂—⟨phenyl⟩ | |
| 549 | CH₃ | H | S | CH₂CH₂ | NHCSNH(CH₂)₂—⟨phenyl⟩ | |
| 550 | CH₃ | H | S | CH₂CH₂ | 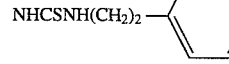 | |
| 551 | CH₃ | H | S | CH₂CH₂ | 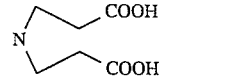 | |
| 552 | CH₃ | H | S | CH₂CH₂ | 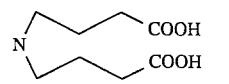 | |
| 553 | CH₃ | H | S | CH₂CH₂ | 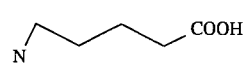 | |
| 554 | CH₃ | H | S | CH₂CH₂ | 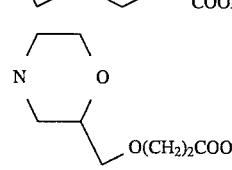 | |
| 555 | CH₃ | H | S | CH₂CH₂ | 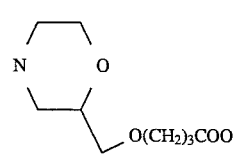 | |

TABLE 6-continued

[Structure: benzimidazole-S-CH₂-pyridine with R² at position 3, R³ at position 5, and B-D-E substituent at position 4]

| No | R² | R³ | B | D | E | MP (°C.) |
|---|---|---|---|---|---|---|
| 556 | CH₃ | H | S | CH₂CH₂ | morpholin-2-yl-CH₂-NH(CH₂)₃COOH | |
| 557 | CH₃ | H | S | CH₂CH(COOH) | NH—Me | |
| 558 | CH₃ | H | S | CH₂CH(COOH) | NHCH₂-phenyl | |
| 559 | CH₃ | H | S | CH₂CH(COOH) | N(Me)(CH₂-phenyl) | |
| 560 | CH₃ | H | S | CH₂CH(COOH) | piperidin-1-yl | |
| 561 | CH₃ | H | S | CH₂CH(COOH) | 4-benzylpiperazin-1-yl | |
| 562 | CH₃ | H | S | CH₂CH(COOH) | 4-methylpiperazin-1-yl | |
| 563 | CH₃ | H | S | CH₂CH(COOH) | 6,7-dimethoxy-1,2,3,4-tetrahydroisoquinolin-2-yl | |
| 564 | CH₃ | H | S | CH₂CH(COOEt) | 1,2,3,4-tetrahydroisoquinolin-2-yl | |
| 565 | CH₃ | H | S | CH₂CH(COOEt) | morpholin-4-yl | |
| 566 | CH₃ | H | S | CH₂CH₂ | NH—COOEt | |
| 567 | CH₃ | H | S | CH₂CH₂ | N(Me)(COOEt) | |
| 568 | CH₃ | H | S | CH₂CH₂ | N(CH₂-phenyl)(COOEt) | |

TABLE 6-continued
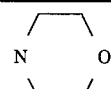
| No | R² | R³ | B | D | E | MP (°C.) |
|---|---|---|---|---|---|---|
| 569 | H | H | S | CH₂CH₂ | 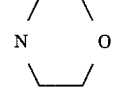 0.2 oxalate | 157–158 |
TABLE 7
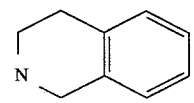
| No | P | Q | B | D | E | MP (°C.) |
|---|---|---|---|---|---|---|
| 601 | CH | N | S | CH₂CH₂ | 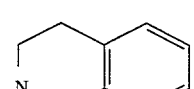 | 218–219 |
| 602 | N | CH | S | CH₂CH₂ | 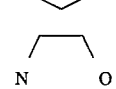 | |
| 603 | CH | N | S | CH₂CH₂ | 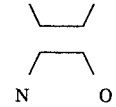 | |
| 604 | N | CH | S | CH₂CH₂ | 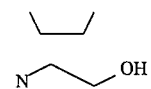 | |
| 605 | CH | N | S | (CH₂)₃ | 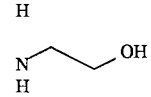 | |
| 606 | CH | N | S | (CH₂)₄ | 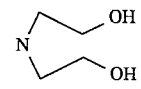 | |
| 607 | CH | N | S | CH₂CH₂ |  | |
| 608 | N | CH | S | CH₂CH₂ | | |
| 609 | CH | N | S | CH₂CH₂ | | |
| 610 | N | CH | S | CH₂CH₂ | | |

TABLE 7-continued

[Structure: imidazo-pyridine-N-oxide linked via S-CH₂ to methylpyridine with B-D-E substituent]

| No | P | Q | B | D | E | MP (°C.) |
|---|---|---|---|---|---|---|
| 611 | CH | N | S | CH₂CH₂ | N(Me)CH₂CH₂OH | |
| 612 | N | CH | S | CH₂CH₂ | N(Me)CH₂CH₂OH | |
| 613 | CH | N | S | CH₂CH₂ | N-CH₂-C₆H₄-COOH (benzyl with COOH) | |
| 614 | N | CH | S | CH₂CH₂ | N-CH₂-C₆H₄-COOH | |
| 615 | CH | N | S | CH₂CH₂ | N(Me)CH₂COOH | |
| 616 | N | CH | S | CH₂CH₂ | N(Me)CH₂COOH | |
| 617 | CH | N | S | CH₂CH₂ | N(Me)CH₂CH₂COOH | |
| 618 | N | CH | S | CH₂CH₂ | N(Me)CH₂CH₂COOH | |
| 619 | CH | N | S | CH(Et)CH(OH)Et (pentan-3-ol branch) | NH—Et | |
| 620 | N | CH | S | CH₂CH(COOH) | NH₂ | |
| 621 | CH | CH | S | CH₂CH₂ | piperazinyl-N-CH₂CH₂OH | 217–220 |
| 622 | CH | CH | S | CH₂CH₂ | 2-methylpiperazinyl-N-COCH₃ | |

EXAMPLE 1001

A metallic sodium (3.86 g) was placed in ethanol (300 ml) and 2,3-dimethyl-4-mercaptopyridine-N-oxide (23.7 g) was added thereto with stirring at room temperature. The mixture was stirred at 50° C. for 15 minutes. Polyethylene glycol monomethyl ether (average molecular weight 350) was reacted with thionyl chloride by a conventional method to give 56.2 g of 2-methoxypolyethoxy ethyl chloride which was added to the above-mentioned reaction mixture. The mixture was refluxed with stirring for 2 hours. After the completion of the reaction, the reaction mixture was concentrated under reduced pressure and added with water. The mixture was extracted with ethyl acetate. The ethyl acetate layer was dried over anhydrous magnesium sulfate and concentrated under reduced pressure to give 74 g of 2,3-dimethyl-4-(2-(2-methoxypolyethoxy)ethylthio)pyridine-N-oxide (derived from polyethylene glycol monomethyl ether having an average molecular weight of 350) as a pale yellow oily substance.

$^1$H-NMR (CDCl$_3$): δ (ppm)=2.35 (s,3H), 2.52 (s,3H), 3.17 (t,2H), 3.38 (s,3H), 3.45–3.8 (m), 7.05 (d,1H), 8.05 (d,1H)

In the same manner as above, the following compounds were obtained.

EXAMPLE 1002

2,3-Dimethyl-4-(2-(2-methoxyethoxy)ethylthio)pyridine-N-oxide $^1$H-NMR (CDCl$_3$): δ (ppm)=2.35 (s,3H), 2.55 (s,3H), 3.17 (t,2H), 3.40 (s,3H), 3.52–3.8 (m,6H), 7.05 (d,1H), 8.05 (d,1H)

EXAMPLE 1003

2,3-Dimethyl-4-(2-(2-(2-methoxyethoxy)thoxy)ethylthio)pyridine-N-oxide $^1$H-NMR (CDCl$_3$): δ (ppm)=2.35 (s,3H), 2.55 (s,3H), 3.17 (t,2H), 3.38 (s,3H), 3.45–3.8 (m, 10H), 7.05 (d,1H), 8.05 (d,1H)

EXAMPLE 1004

2,3-Dimethyl-4-(2-(2-methoxypolyethoxy)ethylthio)pyridine-N-oxide (derived from polyethylene glycol monomethyl ether having an average molecular weight of 550)

$^1$H-NMR (CDCl$_3$): 67 (ppm)=2.25 (s,3H), 2.35 (s,3H), 3.20 (t,2H), 3.35 (s,3H), 3.45–3.6 (m), 7.2 (d,1H), 8.05 (d,1H)

EXAMPLE 1005

2,3-Dimethyl-4-(2-(2-methoxypolyethoxy)ethylthio)pyridine-N-oxide (derived from polyethylene glycol monomethyl ether having an average molecular weight of 750)

$^1$H-NMR (CDCl$_3$): δ (ppm)=2.35 (s,3H), 2.55 (t,2H), 3.15 (t,2H), 3.35 (s,3H), 3.50–3.75 (m), 7.05 (d,1H), 8.10 (d,1H)

EXAMPLE 1006

2,3-Dimethyl-4-(2-(2-methoxypolyethoxy)ethylthio)pyridine-N-oxide (7.2 g, derived from polyethylene glycol monomethyl ether having an average molecular weight of 350) was dissolved in acetic anhydride (30 ml) and the mixture was stirred at 90° C. for 2 hours. The solvent was distilled away and water was added to the residue. The mixture was extracted with chloroform and dried over anhydrous magnesium sulfate. The solvent was distilled away. The obtained residue, 2-acetoxymethyl-3-methyl-4-(2-(2-methoxypolyethoxy)ethylthio)pyridine, was dissolved in ethanol (80 ml) and thereto was added sodium hydroxide (0.9 g) dissolved in water (10 ml). The mixture was refluxed under stirring for 1 hour. After the completion of the reaction, the ethanol was distilled away and the residue was extracted with ethyl acetate. The ethyl acetate layer was dried over anhydrous magnesium sulfate and the solvent was distilled away. The obtained residue was subjected to silica gel column chromatography and eluted with chloroform-methanol=98:2 to give 4.6 g of 3-methyl-4-(2-(2-methoxypolyethoxy)ethylthio)pyridine-2-methanol (derived from polyethylene glycol monomethyl ether having an average molecular weight of 350) as a pale yellow oily substance.

$^1$H-NMR (CDCl$_3$): δ (ppm)=2.15 (s,3H), 3.20 (t,2H), 3.39 (s,3H), 3.45–3.85 (m), 4.48 (s,2H), 7.05 (d,1H), 8.25 (d,1H)

In the same manner as above, the following compounds were obtained.

EXAMPLE 1007

3-Methyl-4-(2-(2-methoxyethoxy)ethylthio)pyridine-2-methanol $^1$H-NMR (CDCl$_3$): δ (ppm)=2.15 (s,3H), 3.2 (t,3H), 3.4 (s,3H), 3.52 (t,2H), 3.65 (t,2H), 3.75 (t,2H), 4.65 (s,2H), 7.05 (d,1H), 8.23 (d,1H)

EXAMPLE 1008

3-Methyl-4-(2-(2-(2-methoxyethoxy)ethoxy)ethylthio)pyridine-2-methanol $^1$H-NMR (CDCl$_3$): δ (ppm)=2.15 (s,3H), 3.2 (t,2H), 3.39 (s,3H), 3.45–3.85 (m, 10H), 4.65 (s,2H), 7.05 (d,1H), 8.25 (d,1H)

EXAMPLE 1009

3-Methyl-4-(2-(2-methoxypolyethoxy)ethylthio)pyridine-2-methanol (derived from polyethylene glycol monomethyl ether having an average molecular weight of 350)

$^1$H-NMR (CDCl$_3$): δ (ppm)=2.15 (s,3H), 3.2 (t,2H), 3.39 (s,3H), 3.5–3.8 (m), 4.68 (s,2H), 7.1 (d,1H), 8.25 (d,1H)

EXAMPLE 1010

3-Methyl-4-(2-(2-methoxypolyethoxy)ethylthio)pyridine-2-methanol (derived from polyethylene glycol monomethyl ether having an average molecular weight of 550)

$^1$H-NMR (d6-DMSO): δ (ppm)=2.2 (s,3H), 3.25 (t,2H), 3.3 (s,3H), 3.4–3.8 (m), 4.53 (d,1H), 5.0 (t,1H), 7.22 (d,1H), 8.2 (d,1H)

EXAMPLE 1011

3-Methyl-4-(2-(2-methoxypolyethoxy)ethylthio)pyridine-2-methanol (derived from polyethylene glycol monomethyl ether having an average molecular weight of 750)

$^1$H-NMR (d6-DMSO ): δ (ppm)=2.13 (s,3H), 3.23 (t,2H), 3.38 (s,3H), 3.5–3.8 (m), 3.70 (s,2H), 7.08 (d,1H), 8.25 (d,1H)

EXAMPLE 1012

3-Methyl-4-(2-(2-methoxyethoxy)ethylthio)pyridine-2-methanol (10 g) was dissolved in chloroform (50 ml) and thionyl chloride (3.1 ml) was dropwise added thereto under ice-cooling. The mixture was stirred at room temperature for 1.5 hours. After the completion of the reaction, the thionyl chloride was distilled away and the residue was alkali over-saturated with potassium carbonate and extracted with chloroform. The chloroform layer was dried over anhydrous magnesium sulfate and the solvent was distilled away to give 10 g of 2-chloromethyl-3-methyl-4-(2-(2-methoxypolyethoxy)ethylthio)pyridine as an oily substance. The oily substance was added to ethanol (50 ml) containing 2-mercaptobenzimidazole (2.5 g) and sodium hydroxide (0.8 g) dissolved in water (10 ml) and the mixture was refluxed under heating for 2 hours. After the completion of the reaction, the ethanol was distilled away and water was added to the residue, which mixture was extracted with chloroform. The chloroform layer was dried over anhydrous magnesium sulfate and the solvent was distilled away. Ethanolic hydrochloric acid was added to the residue to give a hydrochloride thereof, which was recrystallized from ethanol to give white crystals of 2-((3-methyl-4-(2-(2-methoxyethoxy)ethylthio)-2-pyridyl)methylthio)-1H-benzimidazole hydrochloride, melting point 186°–189° C.

In the same manner as above, the following compounds were obtained.

EXAMPLE 1013

2-((3-Methyl-4-(2-(2-(2-methoxyethoxy)ethoxy)ethylthio)-2-pyridyl)methylthio)-1H-benzimidazole hydrochloride, melting point 181°–183° C.

EXAMPLE 1014

2-((3-Methyl-4-(2-(2-methoxypolyethoxy)ethylthio)-2-pyridyl)methylthio)-1H-benzimidazole hydrochloride (derived from polyethylene glycol monomethyl ether having an average molecular weight of 350).

$^1$H-NMR (CDCl$_3$): δ (ppm)=2.38 (s,3H), 3.39 (s,3H), 3.5–3.8 (m), 4.5 (s,2H), 7.1–7.6 (m,5H), 8.3 (d,1H)

EXAMPLE 1015

2-((3-Methyl-4-(2-(2-methoxypolyethoxy)ethylthio)-2-pyridyl)methylthio)-1H-benzimidazole hydrochloride (derived from polyethylene glycol monomethyl ether having an average molecular weight of 550).

$^1$H-NMR (CDCl$_3$): δ (ppm)=2.38 (s,3H), 3.39 (s,3H), 3.5–3.8 (m), 4.5 (s,2H), 7.1–7.6 (m,5H), 8.3 (d,1H)

EXAMPLE 1016

2-((3-Methyl-4-(2-(2-methoxypolyethoxy)ethylthio)-2-pyridyl)methylthio)-1H-benzimidazole hydrochloride (derived from polyethylene glycol monomethyl ether having an average molecular weight of 750).

$^1$H-NMR (CDCl$_3$): δ (ppm)=2.38 (s,3H), 3.20 (t,2H), 3.38 (s,3H), 3.5–3.85 (m), 4.48 (s,2H), 7.08–7.20 (m,3H), 7.48–7.58 (m,2H), 8.28 (d,1H)

EXAMPLE 1017

2-((3-Methyl-4-(2-(2-methoxypolyethoxy)ethylthio)-2-pyridyl)methylthio)-1H-benzimidazole (1.2 g, derived from polyethylene glycol monomethyl ether having an average molecular weight of 350) was dissolved in chloroform (20 ml) and 80% m-chloroperbenzoate (0.38 g) was added thereto under ice-cooling. The mixture was stirred for 30 minutes under ice-cooling. After the completion of the reaction, the solvent was distilled away and the residue was subjected to alumina column chromatography and eluted with chloroform-methanol=99:1 to give 0.52 g of 2-((3-methyl-4-(2-(2-methoxypolyethoxy)ethylthio)-2-pyridyl)methylsulfinyl)-1H-benzimidazole (derived from polyethylene glycol monomethyl ether having an average molecular weight of 350) as a pale brown oily substance.

$^1$H-NMR (CDCl$_3$): δ (ppm)=2.25 (s,3H), 3.1–3.25 (t,2H), 3.37 (s,3H), 3.4–3.85 (m), 4.8 (d,2H), 7.05 (d,1H), 7.20–7.40 (m,4H), 8.25 (d,1H)

EXAMPLE 1018

2-((3-Methyl-4-(2-(2-methoxypolyethoxy)ethylthio)-2-pyridyl)methylthio)-1H-benzimidazole (1.2 g, derived from polyethylene glycol monomethyl ether having an average molecular weight of 550) was dissolved in chloroform (30 ml) and 80% m-chloroperbenzoate (0.38 g) was added thereto under ice-cooling. The mixture was stirred for 30 minutes under ice-cooling. After the completion of the reaction, the solvent was distilled away and the residue was subjected to alumina column chromatography and eluted with chloroform-methanol=99:1 to give 0.523 g of 2-((3-methyl-4-(2-(2-methoxypolyethoxy)ethylthio)-2-pyridyl)methylsulfinyl)-1H-benzimidazole (derived from polyethylene glycol monomethyl ether having an average molecular weight of 550) as a pale brown oily substance.

$^1$H-NMR (CDCl$_3$): δ (ppm)=2.25 (s,3H), 3.15 (t,2H), 3.37 (s,3H), 3.4–3.75 (m), 3.73 (t,2H), 4.78 (d,2H), 7.06 (d,1H), 7.20–7.40 (m,4H), 8.25 (d,1H)

EXAMPLE 1019

N,N-Dimethylformamide (200 ml) was added to 2,3-dimethyl-4-mercaptopyridine-N-oxide (20 g) and thereto were added diethyl chloroacetal (25 g) and potassium carbonate (20 g). The mixture was stirred at 70°–80° C. for 12 hours. After the completion of the reaction, water was added thereto and the mixture was extracted with ethyl acetate. The ethyl acetate layer was dried over anhydrous magnesium sulfate and the solvent was distilled away. The residue was subjected to silica gel column chromatography and eluted with chloroform-methanol=98:2 to give 28 g of 2,3-dimethyl-4-(2-diethoxyethylthio)pyridine-N-oxide as a pale brown oily substance.

$^1$H-NMR (CDCl$_3$): δ (ppm)=1.20 (t,6H), 2.35 (s,3H), 2.55 (s,3H), 3.15 (d,2H), 3.55 (q,2H), 3.70 (q,2H), 4.70 (t,1H), 7.10 (d,1H), 8.10 (d,1H)

EXAMPLE 1020

2,3-Dimethyl-4-(2-diethoxyethylthio)pyridine-N-oxide (10.8 g) was dissolved in benzene (200 ml) and p-toluenesulfonic acid (7.6 g) was added thereto. The mixture was refluxed with stirring for 2 hours. After the completion of the reaction, the mixture was washed with water and dried over anhydrous magnesium sulfate. The solvent was distilled away and the residue was subjected to silica gel column chromatography and eluted with chloroform-methanol=98:2 to give 2.1 g of trans-2,3-dimethyl-4-(2-ethoxyvinylthio)pyridine-N-oxide as a pale yellow oily substance.

$^1$H-NMR (CDCl$_3$): δ (ppm)=1.30 (t,3H), 2.30 (s,3H), 2.55 (s,3H), 3.15 (d,2H), 4.00 (q,2H), 5.25 (d,1H), 6.85 (d,1H), 7.00 (d,1H), 8.10 (d,1H)

EXAMPLE 1021

In the same manner as in Example 1006, trans-3-methyl-4-(2-ethoxyvinylthio)pyridine-2-methanol was obtained using trans-2,3-dimethyl-4-(2-ethoxyvinylthio)pyridine-N-oxide.

$^1$H-NMR (CDCl$_3$): δ (ppm)=1.35 (t,3H), 2.15 (s,3H), 4.00 (q,2H), 4.65 (s,2H), 5.30 (d,1H), 6.85 (d,1H), 7.10 (d,1H), 8.25 (d,1H)

The following compounds are obtained in the same manner as in Example 1012.

EXAMPLE 1022 trans-2-((3-Methyl-4-(2-ethoxyvinylthio)-2-pyridyl)methylthio-1H-benzimidazole, melting point 185°–188° C. (decomp.)

EXAMPLE 1023

2-((3-Methyl-4-(2-(2-methoxypolyethoxy)ethylthio)-2-pyridyl)methylthio)-3H-imidazo[4,5-b]pyridine (derived from polyethylene glycol monomethyl ether having an average molecular weight of 350)

$^1$H-NMR (CDCl$_3$): δ (ppm)=2.40 (s,3H), 3.20 (t,2H), 3.40 (s,3H), 3.50–3.70 (m), 3.75 (t,2H), 4.50 (s,2H), 7.15 (m,2H), 7.85 (d,1H), 8.30 (d, 1H), 8.35 (d,1H)

EXAMPLE 1024

2-((3-Methyl-4-(2-(2-methoxypolyethoxy)ethylthio)-2-pyridyl)methylthio)-3H-imidazo[4,5-c]pyridine (derived from polyethylene glycol monomethyl ether having an average molecular weight of 350)

$^1$H-NMR (CDCl$_3$): δ (ppm)=2.40 (s,3H), 3.25 (t,2H), 3.40 (s,3H), 3.50–3.70 (m), 3.75 (t,2H), 4.50 (s,2H), 7.15 (d,1H), 7.50 (d,1H), 8.45 (d,1H), 8.48 (d,1H), 8.90 (s,1H)

EXAMPLE 1025

2,3-Dimethyl-4-(2-ethoxyethylthio)pyridine-N-oxide $^1$H-NMR (CDCl$_3$): δ (ppm)=1.20 (t,3H), 2.35 (s,3H), 2.56 (s,3H), 3.15 (t,2H), 3.52 (q,2H), 3.68 (t,2H), 7.04 (d,1H), 8.10 (d,1H)

EXAMPLE 1026

3-Methyl-4-(2-ethoxyethylthio)pyridine-2-methanol $^1$H-NMR (CDCl$_3$): δ (ppm)=1.20 (t,3H), 2.12 (s,3H), 3.20 (t,2H), 3.56 (q,2H), 3.72 (t,2H), 4.66 (s,2H), 7.06 (d,1H), 8.28 (d,1H)

EXAMPLE 1027

2-((3-Methyl-4-(2-ethoxyethylthio)-2-pyridyl)methylthio)-1H-benzimidazole hydrochloride, melting point 191°–194° C. (decomp.)

EXAMPLE 1028

2,3-Dimethyl-4-(2-(2-(2-methoxyethoxy)ethoxy)ethylthio)pyridine-N-oxide $^1$H-NMR (CDCl$_3$): δ (ppm)=2.35 (s,3H), 2.55 (s,3H), 3.17 (t,2H), 3.40 (s,3H), 3.50–3.80 (m,14H), 7.05 (d,1H), 8.05 (d,1H)

EXAMPLE 1029

3-Methyl-4-(2-(2-(2-methoxyethoxy)ethoxy)ethylthio)pyridine-2-methanol $^1$H-NMR (CDCl$_3$): δ (ppm)=2.15 (s,3H), 3.20 (t,2H), 3.40 (s,3H), 3.40–3.80 (m,14H), 4.65 (s,2H), 7.05 (d,1H), 8.25 (d,1H)

EXAMPLE 1030

2-((3-Methyl-4-(2-(2-(2-methoxyethoxy)ethoxy)ethylthio)-2-pyridyl)methylthio)-1H-benzimidazole hydrochloride, melting point 148°–149° C.

EXAMPLE 1031

2-((3-Methyl-4-(4,7,10,13,16-pentaoxa1-thia-heptadecyl)-2-pyridyl)methylthio)-1H-benzimidazole $^1$H-NMR (CDCl$_3$): δ (ppm)=2.37 (s,3H), 3.22 (s,3H), 3.30–3.90 (m,20H), 5.00 (s,2H), 7.30–7.50 (m,2H), 7.55–7.75 (m,3H), 8.3 (d,1H)

EXAMPLE 1032

2-((3-Methyl-4-(4,7,10,13,16,19-hexaoxa1-thia-icosyl)-2-pyridyl)methylthio)-1H-benzimidazole $^1$H-NMR (CDCl$_3$): δ (ppm)=2.37 (s,3H), 3.2 (s,3H), 3.34–3.85 (m,24H), 4.80 (s,2H), 7.30–7.70 (m,5H), 8.20 (d,1H)

EXAMPLE 1033

2-((3-Methyl-4-(4,7,10,13,16,19,22-heptaoxa-1-thiatricosyl)-2-pyridyl)methylthio)-1H-benzimidazole $^1$H-NMR (CDCl$_3$): δ (ppm)=2.38 (s,3H), 3.35 (s,3H), 3.4–3.85 (m,28H), 4.70 (s,2H), 7.20–7.65 (m,5H), 8.25 (d,1H)

EXAMPLE 1034

2-((3-Methyl-4-(4,7,10,13,16,19,22,25-octaoxa-1-thia-hexacosyl)-2-pyridyl)methylthio)-1H-benzimidazole $^1$H-NMR (CDC$_3$): δ (ppm)=2.38 (s,3H), 3.38 (s,3H), 3.5–3.8 (m,32H), 4.5 (s,2H), 7.10–7.62 (m,5H), 8.3 (d,1H)

EXAMPLE 1035

2-((3-Methyl-4-(2-hydroxyethylthio)-2-pyridyl)methylthio)-1H-benzimidazole melting point 106°–108° C.

The compounds obtained in the above Examples are shown in Tables 8 and 9. In the Tables, Me means methyl, Et means ethyl, Pr means propyl, Bu means butyl and ca. means circa (about).

TABLE 8

| Example | P | Q | R$^1$ | R$^2$ | R$^3$ | R$^4$ | R$^5$ | B | n | q |
|---|---|---|---|---|---|---|---|---|---|---|
| 1012 | CH | CH | H | 3-Me | H | H | Me | 4-S | 0 | 2 |
| 1013 | CH | CH | H | 3-Me | H | H | Me | 4-S | 0 | 3 |
| 1014 | CH | CH | H | 3-Me | H | H | Me | 4-S | 0 | ca.7 |
| 1015 | CH | CH | H | 3-Me | H | H | Me | 4-S | 0 | ca.12 |
| 1016 | CH | CH | H | 3-Me | H | H | Me | 4-S | 0 | ca.16 |
| 1017 | CH | CH | H | 3-Me | H | H | Me | 4-S | 1 | ca.7 |
| 1018 | CH | CH | H | 3-Me | H | H | Me | 4-S | 1 | ca.12 |
| 1023 | CH | N | H | 3-Me | H | H | Me | 4-S | 0 | ca.7 |
| 1024 | N | CH | H | 3-Me | H | H | Me | 4-S | 0 | ca.7 |
| 1027 | CH | CH | H | 3-Me | H | H | Et | 4-S | 0 | 1 |
| 1030 | CH | CH | H | 3-Me | H | H | Me | 4-S | 0 | 4 |
| 1031 | CH | CH | H | 3-Me | H | H | Me | 4-S | 0 | 5 |
| 1032 | CH | CH | H | 3-Me | H | H | Me | 4-S | 0 | 6 |
| 1033 | CH | CH | H | 3-Me | H | H | Me | 4-S | 0 | 7 |
| 1034 | CH | CH | H | 3-Me | H | H | Me | 4-S | 0 | 8 |
| 1035 | CH | CH | H | 3-Me | H | H | H | 4-S | 0 | 1 |

TABLE 9

$R^1$, $R^2$, $R^3$, $R^4$, $R^5$, B, P, Q, n, q structure with B(CH=CH—O)$_q$R$^5$ group

| Example | P | Q | R¹ | R² | R³ | R⁴ | R⁵ | B | n | q |
|---|---|---|---|---|---|---|---|---|---|---|
| 1022 | CH | CH | H | 3-Me | H | H | Et | 4-S | 0 | 1 |

In the same manner as in the above Examples, the compounds of Tables 10 to 13 can be obtained.

TABLE 10

Structure with B—(CH$_2$CH$_2$O)$_q$—R$^5$ group

| Example | P | Q | R¹ | R² | R³ | R⁴ | R⁵ | B | n | q |
|---|---|---|---|---|---|---|---|---|---|---|
| 1101 | CH | CH | H | 3-Me | H | CH₂OH | Me | 4-S | 0 | ca.12 |
| 1102 | CH | CH | H | 3-Me | H | H | Me | 4-SO | 0 | ca.7 |
| 1103 | CH | CH | H | 3-Me | H | H | Me | 4-SO | 0 | ca.12 |
| 1104 | CH | CH | H | 3-Me | H | H | Me | 4-SO₂ | 0 | ca.7 |
| 1105 | CH | CH | H | 3-Me | H | H | Me | 4-SO₂ | 0 | ca.12 |
| 1106 | CH | CH | H | 3-Me | H | H | Me | 4-S | 2 | 4 |

TABLE 11

Structure with B—(CH$_2$CH$_2$O)$_q$—R$^5$ group

| Example | P | Q | R¹ | R² | R³ | R⁴ | R⁵ | B | n | q |
|---|---|---|---|---|---|---|---|---|---|---|
| 1107 | CH | CH | H | 3-Me | H | H | Me | 4-S | 0 | 9 |
| 1108 | CH | CH | H | 3-Me | H | H | Me | 4-S | 0 | 10 |
| 1109 | CH | CH | H | 3-Me | H | H | Me | 4-S | 0 | 11 |
| 1110 | CH | CH | H | H | H | H | Me | 4-S | 0 | ca.7 |
| 1111 | CH | CH | H | H | H | H | Me | 4-S | 1 | ca.7 |
| 1112 | CH | CH | H | 3-Me | H | H | Me | 4-S | 1 | 4 |
| 1113 | CH | CH | H | 3-Me | H | H | Me | 4-S | 1 | 5 |
| 1114 | CH | CH | H | 3-Me | H | H | Me | 4-S | 1 | 6 |
| 1115 | CH | CH | H | 3-Me | H | H | Me | 4-S | 1 | 8 |

TABLE 12

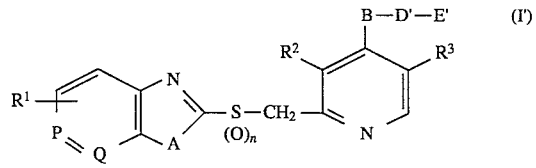

| Example | P | Q | R¹ | R² | R³ | R⁴ | R⁵ | B | n | q |
|---|---|---|---|---|---|---|---|---|---|---|
| 1116 | CH | CH | H | 3-Me | 5-Me | H | Me | 4-S | 0 | ca.7 |
| 1117 | CH | CH | H | 3-Me | 5-Me | H | Me | 4-S | 0 | ca.7 |
| 1118 | CH | CH | 5-OMe | 3-Me | H | H | Me | 4-S | 0 | ca.7 |
| 1119 | CH | CH | 5-OH | 3-Me | H | H | Me | 4-S | 0 | ca.7 |
| 1120 | CH | CH | H | 3-Me | 5-Me | H | Me | 4-S | 0 | ca.7 |
| 1121 | CH | CH | H | 3-Me | 5-Me | COOEt | Me | 4-S | 0 | ca.7 |
| 1122 | CH | CH | 5-F | 3-Me | H | H | Me | 4-S | 0 | 3 |
| 1123 | CH | CH | H | 3-Me | H | H | Me | 4-S | 1 | 2 |
| 1124 | CH | CH | H | 3-Me | H | H | Me | 4-S | 1 | 3 |
| 1125 | CH | CH | H | 3-Me | H | H | Me | 4-S | 0 | 1 |

TABLE 13

| Example | P | Q | R¹ | R² | R³ | R⁴ | R⁵ | B | n | q |
|---|---|---|---|---|---|---|---|---|---|---|
| 1201 | CH | CH | H | 3-Me | H | H | Me | 4-S | 0 | 1 |
| 1202 | CH | CH | H | 3-Me | H | H | Me | 4-S | 0 | 1 |
| 1203 | CH | CH | H | 3-Me | H | H | Pr | 4-S | 0 | 1 |
| 1204 | CH | CH | H | 3-Me | H | H | Bu | 4-S | 0 | 1 |
| 1205 | CH | CH | H | H | H | H | Et | 4-S | 0 | 1 |
| 1206 | CH | CH | H | 3-Me | 5-Me | H | Et | 4-S | 0 | 1 |
| 1207 | CH | N | H | 3-Me | H | H | Et | 4-S | 0 | 1 |
| 1208 | CH | CH | H | 3-Me | H | H | Et | 4-S | 1 | 1 |

Formulation Examples

Tablets

The tablets containing 20 mg of the active ingredient are prepared according to the following formulation.

| | |
|---|---|
| Compound (I) | 20 mg |
| Corn starch | 15 mg |
| Lactose | 57 mg |
| Microcrystalline cellulose | 25 mg |
| Magnesium stearate | 3 mg |
| | 120 mg |

Capsules

The capsules containing 20 mg of the active ingredient are prepared according to the following formulation.

| | |
|---|---|
| Compound (I) | 20 mg |
| Corn starch | 30 mg |
| Lactose | 63 mg |
| Hydroxypropylcellulose | 6 mg |
| Magnesium stearate | 1 mg |
| | 120 mg |

While the present invention has been adequately and fully explained by the foregoing specification and examples included therein, it is subject to changes and modifications as long as they fall within the spirit and scope of the present invention.

What is claimed is:

1. A method for preventing or treating various diseases caused by the bacteria belonging to the genus Helicobacter, which comprises administering to a patient in need of treatment a pyridine compound of formula (I')

$$\text{(I')}$$

wherein $R^1$ is a hydrogen, a halogen, an alkyl, an alkoxy, a hydroxyl, an alkoxycarbonyl, a carboxyl, a haloalkyl, a nitro, an amino, a mono- or dialkylamino, an alkoxycarbonylalkylamino or a carboxyalkylamino, $R^2$ and $R^3$ are the same or different and each is a hydrogen, a halogen or an alkyl, —P=Q— is —CH=CH—, A is an oxygen atom, a sulfur atom or N($R^4$), wherein $R^4$ is hydrogen, alkyl, alkoxycarbonyl, hydroxyalkyl, alkoxyalkyl, acyloxyalkyl, alkoxycarbonylalkyl, carboxyalkyl, carbamoyl, carbamoylalkyl, mono- or dialkylcarbamoyl, mono- or dialkylcarbamoylalkyl, thiocarbamoyl, or mono- or dialkylthiocarbamoyl, n is 0, 1 or 2, B is S(O)p, wherein p is 0, 1 or 2, D' is a single bond, an alkylene, an alkylene having substituent or an alkylene having oxo, and E' is an alkoxyalkyl, a group of the formula (a), $$-N\begin{matrix}R^6\\R^7\end{matrix} \quad (a)$$

wherein $R^6$ and $R^7$ are the same or different and each is hydrogen, alkyl, cycloalkyl, acyl, alkoxycarbonyl, carbamoyl, mono- or dialkylcarbamoyl, optionally substituted phenylcarbamoyl, thiocarbamoyl, mono- or dialkylthiocarbamoyl, optionally substituted phenylthiocarbamoyl, hydroxyalkyl, alkoxycarbonylaklyl, optionally substituted phenylalkylcarbamoyl, optionally substituted phenylalkylthiocarbamoyl, carboxyalkyl, optionally substituted phenyl, optionally substituted phenylalkyl or optionally substituted heteroarylalkyl, or $R^6$ and $R^7$ may form, together with the adjoining nitrogen atom, an optionally condensed and optionally substituted heterocyclic ring, or a group of the formula (b)

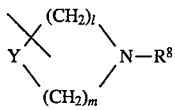

wherein $R^8$ is hydrogen, alkyl, acyl, carboxyalkyl or optionally substituted phenylalkyl, Y is methylene, oxygen atom or sulfur atom and l and m are the same or different and each is 0 or an integer of 1 to 3;

or a pharmaceutically acceptable salt thereof as an active ingredient.

2. A method for preventing or treating gastrointestinal diseases, which comprises administering to a patient in need of treatment a pyridine compound of formula (I')

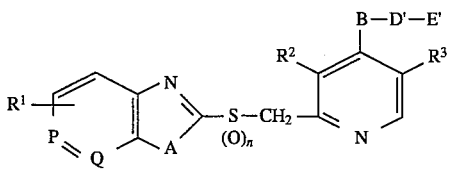

wherein $R^1$ is a hydrogen, a halogen, an alkyl, an alkoxy, a hydroxyl, an alkoxycarbonyl, a carboxyl, a haloalkyl, a nitro, an amino, a mono- or dialkylamino, an alkoxycarbonylalkylamino or a carboxyalkylamino, $R^2$ and $R^3$ are the same or different and each is a hydrogen, a halogen or an alkyl, —P=Q— is —CH=CH—, A is an oxygen atom, a sulfur atom or N($R^4$), wherein $R^4$ is hydrogen, alkyl, alkoxycarbonyl, hydroxyalkyl, alkoxyalkyl, acyloxyalkyl, alkoxycarbonylalkyl, carboxyalkyl, carbamoyl, carbamoylalkyl, mono- or dialkylcarbamoyl, mono- or dialkylcarbamoylalkyl, thiocarbamoyl, or mono- or dialkylthiocarbamoyl, n is 0, 1 or 2, B is S(O)p, wherein p is 0, 1 or 2, D' is a single bond, an alkylene, an alkylene having substituent or an alkylene having oxo, and E' is an alkoxyalkyl, a group of the formula (a),

wherein $R^6$ and $R^7$ are the same or different and each is hydrogen, alkyl, cycloalkyl, acyl, alkoxycarbonyl, carbamoyl, mono- or dialkylcarbamoyl, optionally substituted phenylcarbamoyl, thiocarbamoyl, mono- or dialkylthiocarbamoyl, optionally substituted phenylthiocarbamoyl, hydroxyalkyl, alkoxycarbonylalkyl, optionally substituted phenylalkylcarbamoyl, optionally substituted phenylalkylthiocarbamoyl, carboxyalkyl, optionally substituted phenyl, optionally substituted phenylalkyl or optionally substituted heteroarylalkyl, or $R^6$ and $R^7$ may form, together with the adjoining nitrogen atom, an optionally condensed and optionally substituted heterocyclic ring, or a group of the formula (b)

wherein $R^8$ is hydrogen, alkyl, acyl, carboxyalkyl or optionally substituted phenylalkyl, Y is methylene, oxygen atom or sulfur atom and l and m are the same or different and each is 0 or an integer of 1 to 3;

or a pharmaceutically acceptable salt thereof as an active ingredient.

3. The method of claim 1, wherein the pyridine compound is selected from the group consisting of 2-((3-methyl-4-(2-morpholinoethylthio)-2-pyridyl)methylthio)-1H-benzimidazole, 2-((3-methyl-4-(2-(1,2,3,4-tetrahydroisoquinolin-2-yl)ethylthio)-2-pyridyl)methylthio)-1H-benzimidazole, 2-((4-(2-(N-benzyl-N-methylamino)ethylthio)-3-methyl-2-pyridyl)methylthio)-1H-benzimidazole, 2-((4-(1-benzyl-4-piperidyl)thio-3-methyl-2-pyridyl)methylthio)-1H-benzimidazole, ethyl 2-((3-methyl-4-(2-morpholinoethylthio)-2-pyridyl)methylthio)-1H-benzimidazole-1-carboxylate, methyl 2-((3-methyl-4-(2-(1,2,3,4-tetrahydroisoquinolin-2-yl)-ethylthio)-2-pyridyl)methylthio)-1H-benzimidazole-1-carboxylate, 4-(2-((2-(1H-benzimidazole-2-yl)thiomethyl-3-methyl-4-pyridyl)-thio)ethyl)morpholine N-oxide, 2-((3-methyl-4-(2-acetylaminoethylthio)-2-pyridyl)methylthio)-1H-benzimidazole, 2-((3-methyl-4-(2-benzylaminoethylthio)-2-pyridyl)methylthio)-1H-benzimidazole, 2-((3-methyl-4-(2-(2-hydroxyethylamino)ethylthio)-2-pyridyl)methylthio)-1H-benzimidazole, 2-((3-methyl-4-(2-(N,N-di(2-hydroxyethyl)amino)ethylthio)-2-pyridyl)methylthio)-1H-benzimidazole, 2-((3-methyl-4-(2-(2-carboxyethylamino)ethylthio)-2-pyridyl)methylthio)-1H-benzimidazole, 2-((3-methyl-4-(2-morpholino-2-carboxyethylthio)-2-pyridyl)methylthio)-1H-benzimidazole, 2-((3-methyl-4-(2-dimethylaminoethylthio)-2-pyridyl)methylthio)-1H-benzimidazole and 2-((3-methyl-4-(2-(1-acetyl-2-methyl-4-piperazinyl)ethylthio)-2-pyridyl)methylthio)-1H-benzimidazole, or a pharmaceutically acceptable salt thereof.

4. The method of claim 2, wherein the pyridine compound is selected from the group consisting of 2-((3-methyl-4-(2-morpholinoethylthio)-2-pyridyl)methylthio)-1H-benzimidazole, 2-((3-methyl-4-(2-(1,2,3,4-tetrahydroisoquinolin-2-yl)ethylthio)-2-pyridyl)methylthio)-1H-benzimidazole, 2-((4-(2-(N-benzyl-N-methylamino)ethylthio)-3-methyl-2-pyridyl)methylthio)-1H-benzimidazole, 2-((4-(1-benzyl-4-piperidyl)thio-3-methyl-2-pyridyl)methylthio)-1H-benzimidazole, ethyl 2-((3-methyl-4-(2-morpholinoethylthio)-2-pyridyl)methylthio)-1H-benzimidazole-1-carboxylate, ethyl 2-((3-methyl-4-(2-(1,2,3,4-tetrahydroisoquinolin-2-yl)-ethylthio)-2-pyridyl)methylthio)-1H-benzimidazole-1-carboxylate, 4-(2-((2-(1H-benzimidazole-2-yl)thiomethyl-3-methyl-4pyridyl)-thio)ethyl)morpholine N-oxide, 2-((3-methyl-4-(2-acetylaminoethylthio)-2-pyridyl)methylthio)-1H-benzimidazole, 2-((3-methyl-4-(2-benzylaminoethylthio)-2-pyridyl)methylthio)-1H-benzimidazole, 2-((3-methyl-4-(2-(2-hydroxyethylamino)ethylthio)-2-pyridyl)methylthio)-1H-benzimidazole, 2-((3-methyl-4-(2-(N,N-di(2-hydroxyethyl)amino)ethylthio)-2-pyridyl)methylthio)-1H-benzimidazole, 2-((3-methyl-4-(2-(2-carboxyethylamino)ethylthio)-2-pyridyl)methylthio)-1H-benzimidazole, 2-((3-methyl-4-(2-morpholino-2-carboxyethylthio)-2-pyridyl)methylthio)-1H-benzimidazole, 2-((3-methyl-4-(2-dimethylaminoethylthio)-2-pyridyl)methylthio)-1H-benzimidazole and 2-((3-methyl-4-(2-(1-acetyl-2-methyl-4-piperazinyl)ethylthio)-2-pyridyl)methylthio)-1H-benzimidazole, or a pharmaceutically acceptable salt thereof.

* * * * *